United States Patent
Kopperdahl et al.

(10) Patent No.: US 9,936,934 B2
(45) Date of Patent: Apr. 10, 2018

(54) QUANTITATIVE PHANTOMLESS CALIBRATION OF COMPUTED TOMOGRAPHY SCANS

(71) Applicant: O.N.Diagnostics, LLC, Berkeley, CA (US)

(72) Inventors: David L. Kopperdahl, Berkeley, CA (US); David Choen Lee, Arcadia, CA (US); Tony M. Keaveny, Berkeley, CA (US)

(73) Assignee: O.N.Diagnostics, LLC, Berkeley, CA (US)

( * ) Notice: Subject to any disclaimer, the term of this patent is extended or adjusted under 35 U.S.C. 154(b) by 874 days.

(21) Appl. No.: 14/311,242

(22) Filed: Jun. 21, 2014

(65) Prior Publication Data

US 2014/0376701 A1    Dec. 25, 2014

Related U.S. Application Data

(60) Provisional application No. 61/838,159, filed on Jun. 21, 2013.

(51) Int. Cl.
*A61B 6/00* (2006.01)
*A61B 6/03* (2006.01)

(52) U.S. Cl.
CPC .............. *A61B 6/582* (2013.01); *A61B 6/032* (2013.01); *A61B 6/505* (2013.01); *A61B 6/5211* (2013.01)

(58) Field of Classification Search
CPC ........ A61B 6/032; A61B 6/5211; A61B 6/582
See application file for complete search history.

(56) References Cited

U.S. PATENT DOCUMENTS

| | | |
|---|---|---|
| 4,788,706 A | 11/1988 | Jacobson |
| 5,068,788 A | 11/1991 | Goodenough et al. |
| 5,172,695 A | 12/1992 | Cann et al. |
| 6,990,222 B2 | 1/2006 | Arnold |
| 7,292,721 B2 | 11/2007 | Arnold |

(Continued)

OTHER PUBLICATIONS

Agatston, A.S., W.R. Janowitz, F.J. Hildner, N.R. Zusmer, M. Viamonte, Jr., and R. Detrano, Quantification of coronary artery calcium using ultrafast computed tomography. J Am Coll Cardiol, 1990. 15(4): p. 827-32.

(Continued)

*Primary Examiner* — Glen Kao
(74) *Attorney, Agent, or Firm* — Patent Law Offices of Michael E. Woods; Michael E. Woods

(57) ABSTRACT

An apparatus, method, and computer program product for calibrating a CT scan without the use of an external calibration phantom, to enable quantitative assessment of internal body tissues and organs and additionally for any application that would benefit from a calibration of the scan attenuation data, such as viewing CT images in a consistent fashion. Embodiments are described with applications to quantitative assessment of bone density in the spine and hip, mineral content in blood vessels, hepatic-fat content in the liver, and gray-to-white matter ratio in the brain. The primary advantages of the method are that it does not require the use of an external calibration phantom, it is robust across different CT machines and scanner settings, and it is also highly precise, lending itself to a high degree of automation.

27 Claims, 4 Drawing Sheets

(56) References Cited

U.S. PATENT DOCUMENTS

| | | |
|---|---|---|
| 7,424,142 B2 | 9/2008 | Arnold |
| 7,822,253 B2 | 10/2010 | Joshi et al. |
| 8,126,234 B1 | 2/2012 | Edwards et al. |
| 8,517,608 B1 | 8/2013 | Arnold |
| 2003/0095695 A1 | 5/2003 | Arnold |
| 2003/0112921 A1 | 6/2003 | Lang et al. |
| 2011/0116606 A1* | 5/2011 | Yankelevitz ......... A61B 5/1075 378/207 |
| 2011/0213242 A1 | 9/2011 | Budoff et al. |

OTHER PUBLICATIONS

Aslam, R., J. Yee, A. Keedy, T. Joseph, and A. Chau. Assessment of bone mineral density on CT colonography. in SSG13-09 Proc 94th Scientific Assembly and Annual Meeting. 2008. Chicago: Radiological Society of North America.

Augustine, K., J. Camp, D. Holmes, P. Huddleston, L. Lu, M. Yaszemski, and R. Robb, Fracture risk assessment: improved evaluation of vertebral integrity among metastatic cancer patients to aid in surgical decision-making. SPIE Proceedings, 2012. 8317.

Bauer, J.S., S. Virmani, and D.K. Mueller, Quantitative CT to assess bone mineral density as a diagnostic tool for osteoporosis and related fractures, P. Healthcare, Editor 2010.

Bauer, J.S., T.D. Henning, D. Mueller, Y. Lu, S. Majumdar, and T.M. Link, Volumetric quantitative CT of the spine and hip derived from contrast-enhanced MDCT: conversion factors. Am J Roentgenol, 2007. 188(5): p. 1294-301.

Boden, S.D., D.J. Goodenough, C.D. Stockham, E. Jacobs, T. Dina, and R.M. Allman, Precise measurement of vertebral bone density using computed tomography without the use of an external reference phantom. J Digit Imaging, 1989. 2(1): p. 31-8.

Budoff, M.J., J. Takasu, R. Katz, S. Mao, D.M. Shavelle, K.D. O'Brien, R.S. Blumenthal, J.J. Carr, and R. Kronmal, Reproducibility of CT measurements of aortic valve calcification, mitral annulus calcification, and aortic wall calcification in the multiethnic study of atherosclerosis. Acad Radiol, 2006. 13(2): p. 166-72.

Cann, C.E., Quantitative CT applications: comparisons of current scanners. Radiology, 1987. 162: p. 257-261.

Crawley, E.O., W.D. Evans, and G.M. Owen, A theoretical analysis of the accuracy of single-energy CT bone-mineral measurements. Phys Med Biol, 1988. 33(10): p. 1113-27.

Faulkner, K.G., C.E. Cann, and B.H. Hasegawa, Effect of bone distribution on vertebral strength: assessment with patient-specific nonlinear finite element analysis. Radiology, 1991. 179(3): p. 669-74.

Goodsitt, M.M., Beam hardening errors in post-processing dual energy quantitative computed tomography. Med Phys, 1995. 22(7): p. 1039-47.

Gudmundsdottir H et al: "Vertebral Bone Density in Icelandic Women Using Quantitative Computed Tomagraphy Without an External Reference Phantom", Osteoporosis International, XX, XX, vol. 3, No. 2, Mar. 1, 1993 (Mar. 1, 1993).

Hoffmann, U., T.J. Brady, and J. Muller, Cardiology patient page. Use of new imaging techniques to screen for coronary artery disease. Circulation, 2003. 108(8): p. e50-3.

Hopper, K.D., M.P. Wang, and A.R. Kunselman, The use of clinical CT for baseline bone density assessment. J Comput Assist Tomogr, 2000. 24(6): p. 896-9.

International Search Report for International Application No. PCT/US2014/043533 dated Sep. 15, 2014.

Isherwood, I., R.A. Rutherford, B.R. Pullan, and P.H. Adams, Bone-mineral estimation by computer-assisted transverse axial tomography. Lancet, 1976. 2(7988): p. 712-5.

Lenchik, L., R. Shi, T.C. Register, S.R. Beck, C.D. Langefeld, and J.J. Carr, Measurement of trabecular bone mineral density in the thoracic spine using cardiac gated quantitative computed tomography. Journal of Computer Assisted Tomography, 2004. 28(1): p. 134-9.

Ma, X., N.S. Holalkere, R.A. Kambadakone, M. Mino-Kenudson, P.F. Hahn, and D.V. Sahani, Imaging-based quantification of hepatic fat: methods and clinical applications. Radiographics, 2009. 29(5): p. 1253-77.

Mah, P., T.E. Reeves, and W.D. McDavid, Deriving Hounsfield units using grey levels in cone beam computed tomography. Dentomaxillofac Radiol, 2010. 39(6): p. 323-35.

McCullough, E.C., Photon attenuation in computed tomography. Med Phys, 1975. 2(6): p. 307-20.

Metter, R.B., J.C. Rittenberger, F.X. Guyette, and C.W. Callaway, Association between a quantitative CT scan measure of brain edema and outcome after cardiac arrest. Resuscitation, 2011. 82(9): p. 1180-5.

Millner, M.R., W.H. Payne, R.G. Waggener, W.D. McDavid, M.J. Dennis, and V.J. Sank, Determination of effective energies in CT calibration. Medical Physics, 1978. 5(6): p. 543-5.

Miyabara, Y., D. Holmes, 3rd, J. Camp, V.M. Miller, and A.E. Kearns, Comparison of calibrated and uncalibrated bone mineral density by CT to DEXA in menopausal women. Climacteric, 2012. 15(4): p. 374-81.

Mueller, D.K., A. Kutscherenko, H. Bartel, A. Vlassenbroek, P. Ourednicek, and J. Erckenbrecht, Phantom-less QCT BMD system as screening tool for osteoporosis without additional radiation. Eur J Radiol, 2011. 79(3): p. 375-81.

Norton, M.R. and C. Gamble, Bone classification: an objective scale of bone density using the computerized tomography scan. Clin Oral Implants Res, 2001. 12(1): p. 79-84.

Orwoll, E.S., L.M. Marshall, C.M. Nielson, S.R. Cummings, J. Lapidus, J.A. Cauley, K. Ensrud, N. Lane, P.R. Hoffmann, D.L. Kopperdahl, and T.M. Keaveny, Finite element analysis of the proximal femur and hip fracture risk in older men. J Bone Miner Res, 2009. 24(3): p. 475-83.

Pickhardt, P.J., L.J. Lee, A.M. del Rio, T. Lauder, R.J. Bruce, R.M. Summers, B.D. Pooler, and N. Binkley, Simultaneous screening for osteoporosis at CT colonography: bone mineral density assessment using MDCT attenuation techniques compared with the DXA reference standard. J Bone Miner Res, 2011. 26(9): p. 2194-203.

Speliotes, E.K., J.M. Massaro, U. Hoffmann, M.C. Foster, D.V. Sahani, J.N. Hirschhorn, C.J. O'Donnell, and C.S. Fox, Liver fat is reproducibly measured using computed tomography in the Framingham Heart Study. J Gastroenterol Hepatol, 2008. 23(6): p. 894-9.

Summers, R.M., N. Baecher, J. Yao, J. Liu, P.J. Pickhardt, J.R. Choi, and S. Hill, Feasibility of simultaneous computed tomographic colonography and fully automated bone mineral densitometry in a single examination. J Comput Assist Tomogr, 2011. 35(2): p. 212-6.

Takikawa, S., V. Dhawan, P. Spetsieris, W. Robeson, T. Chaly, R. Dahl, D. Margouleff, and D. Eidelberg, Noninvasive quantitative fluorodeoxyglucose PET studies with an estimated input function derived from a population-based arterial blood curve. Radiology, 1993. 188(1): p. 131-6.

Tissue Substitutes in Radiation Dosimetry and Measurement, Report 44 of the International Commission on Radiation Units and Measurements. 1989, Bethesda, Maryland.

Tofts, P.S., Definitions of effective energy in computed tomography. Phys Med Biol, 1981. 26(2): p. 313-7.

Toussaint, N.D., K.K. Lau, B.J. Strauss, K.R. Polkinghorne, and P.G. Kerr, Using vertebral bone densitometry to determine aortic calcification in patients with chronic kidney disease. Nephrology (Carlton), 2010. 15(5): p. 575-83.

Written Opinion of the International Searching Authority for International Application No. PCT/US2014/043533 dated Sep. 15, 2014.

Fidler J, Murthy N, Khosla S, Clarke B, Bruining D, Kopperdahl DL, Lee DC, Keaveny TM: Comprehensive assessment of osteoporosis and bone fragility utilizing computed tomography colonography scans. Radiology, 278:172-80, 2016.

* cited by examiner

100000
QUANTITATIVE PHANTOMLESS CALIBRATION OF COMPUTED TOMOGRAPHY SCANS

CROSS REFERENCE TO RELATED APPLICATIONS

This application claims benefit of U.S. Patent Application No. 61/838,159, the content of which is hereby expressly incorporated in its entirety for all purposes.

FIELD OF THE INVENTION

The present invention relates generally to computed tomography (CT), and more specifically, but not exclusively, to a phantomless calibration of CT scans, without the need for any external calibration phantom, for any application that would benefit from a quantitative calibration of the scan attenuation data, such quantitatively assessing internal body tissues and organs and consistently viewing CT images.

BACKGROUND OF THE INVENTION

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also be inventions.

Quantitative assessment of body tissues and organs from CT (computed tomography) scans represents an important element in many different areas of medicine, for example, in measuring such parameters as bone density or strength at the hip or spine, mineral content in blood vessels, hepatic-fat content in the liver, and gray-to-white matter ratio in the brain. Such quantitative assessments are based in part on some type of quantitative analysis of the X-ray attenuation gray-scale values—commonly referred to as the "CT-numbers"—in the CT scan. The CT-number is usually reported as a Hounsfield Unit (HU), which is a linear scale of X-ray attenuation in which the attenuation of water and air are defined as 0 HU and −1000 HU, respectively. However, calibration of the HU-values or any other type of CT-number is required to correct for inevitable variations in scanner characteristics, beam-hardening, and patient characteristics, any of which can alter the CT-numbers. Without such calibration, for example, the same patient would yield different CT-numbers if imaged on different CT machines or with different scanner settings, confounding the interpretation and clinical utility of the quantitative assessment. When CT scans are calibrated for quantitative assessment, this is commonly referred to as "quantitative CT". The current invention provides improved means of calibration of a CT scan, such improvement facilitating the use of quantitative CT clinically.

The most widely used prior art method of calibration for quantitative CT, used primarily for measurement of bone mineral density, requires the use of some type of external calibration phantom. However, the need for an external calibration phantom, which must be placed under the patient during scanning, adds expense and complexity to the clinical imaging and is therefore not widely used. Another limitation of using an external calibration phantom is that the outcome measures of calibrated density of a tissue are always expressed in terms of the density or concentration of the materials used in the actual phantom; such measures of density are referred to as "equivalent-density" measures. This means that the same tissue for a patient, if measured using different types of external calibration phantoms, may be assigned different values of equivalent-density. This makes clinical interpretation difficult, which hampers widespread clinical adoption of the quantitative CT technology.

To circumvent the need for an external calibration phantom while imaging patients, methods have been developed in which a "pre-calibration" of a particular CT machine is first characterized, typically in some type of research setting using an external calibration phantom, and then that pre-calibration characterization is used clinically for patients without the subsequent need for the external calibration phantom. However, while this method can account for between-machine differences in calibration characteristics for any particular CT machines that are pre-calibrated, it does not account for any patient-specific X-ray attenuation characteristics and thus does not provide a patient-specific calibration; nor it is applicable to CT machines that have not been pre-calibrated or to pre-calibrated CT machines with hardware components that deteriorate over time. A patient-specific phantomless calibration method has been developed in an attempt to address these limitations (U.S. Pat. No. 5,068,788), this method utilizing muscle and fat inside the body as calibration-reference materials. However, since muscle is mixed with fat—and since the ratio of pure fat to pure muscle tissue varies both across patients and within the body—it is difficult to separate out the fat and muscle in a repeatable and reliable fashion. As noted by Pickhardt (2011), these limitations present barriers to clinical use. Combining some aspects of both external-phantom calibration and phantomless calibration, a "hybrid" calibration approach has also been developed (U.S. Pat. Nos. 6,990,222 and 7,292,721). In this approach, an external calibration phantom is used in conjunction with internal body tissues to provide a refinement on the calibration obtained from the external calibration phantom. However, this technique is limited since it also requires the use of an external calibration phantom either before or during imaging the patient.

For certain applications, for example, when measuring bone mineral density, it would also be desirable to be able to use a phantomless calibration technique on CT scans that were acquired using an intravenous contrast agent. Performing a phantomless calibration of such contrast-enhanced CT scans is confounded by the intravenous contrast agent, which is a radio-opaque material injected into the blood. This contrast agent alters the appearance of the blood and (highly perfused) muscle in the CT scan, so these tissues cannot be used as internal reference tissues.

Thus, despite the availability of a number of different approaches to calibrating clinical CT scans with or without an external calibration phantom for use in quantitative CT, there remains a need for a phantomless calibration method that does not require the use of an external calibration phantom, that accounts for machine-specific and patient-specific differences in X-ray attenuation characteristics within the body, that is precise and repeatable, that can be used retrospectively on previously acquired CT scans, and that can sometimes be used in contrast-enhanced scans.

Such a phantomless calibration technique would have widespread clinical utility since it would facilitate implementation of a variety of prior-art quantitative CT applications for which a calibration of the CT scan is desired, but which currently is performed either using no calibration—which has questionable validity as a clinical test—or using one of the prior-art methods of calibration, all of which have their own limitations as noted above. Bone applications include osteoporosis and orthopaedic surgical planning, in which measurements of bone density, bone strength, bone geometry, or bone-implant strength are taken for a specific patient utilizing a patient's CT scan. Non-bone applications include any quantitative assessment of fat or mineral content in soft tissues, a fat-to-liver ratio in the liver in patients with fatty liver disease, measurement of mineral content in blood vessels for cardiovascular assessment, and assessment of the gray-to-white matter ratio in the brains of patients after stroke or cardiac arrest. In addition to these quantitative CT applications, displaying consistent gray-scale values in the CT scan across different CT machines and scanner settings via use of an automated phantomless calibration method can also enhance viewing and qualitative interpretation of CT images.

BRIEF SUMMARY OF THE INVENTION

Disclosed are systems and methods for phantomless calibration of a CT scan that do not require the use of an external calibration phantom and that account for machine-specific and patient-specific differences in X-ray attenuation characteristics within the body. The methods can be used to perform quantitative CT analysis on CT scans obtained without the use of an external calibration phantom, and, in some cases, can be used with contrast-enhanced CT scans. The methods can also be used to calibrate grayscale values in CT scans for the purposes of improving consistency in the appearance of the scan data.

The following summary of the invention is provided to facilitate an understanding of some of technical features related to phantomless calibration for CT scans, and is not intended to be a full description of the present invention. A full appreciation of the various aspects of the invention can be gained by taking the entire specification, claims, drawings, and abstract as a whole. The present invention is applicable to scans obtained from various types of CT scanners, including single-detector CT, multi-detector CT, spiral CT, flat-panel CT, high-resolution peripheral CT, micro-CT, and any CT or radiographic system having image voxels representative of X-ray attenuation. The invention is described as used in single-energy CT scans, which are the most common type of CT exams; it should be obvious to one of ordinary skill in the art that the same embodiments could be adapted to also be used on dual-energy CT exams, or any type of CT exam.

Improved methods are presented for patient-specific, phantomless calibration of CT scans, to be used, for example, in measuring bone mineral density, bone mass, bone volume fraction, assessing bone or bone-implant strength, or quantifying mineral content, including amount of mineral in a blood vessel or in any soft tissue within the body, or measuring fat in the liver, in muscle, or in any other organs, or measuring the relative amount of grey and white matter in the brain, or in any application in which a patient-specific calibration of the attenuation data would be useful, including consistent display and qualitative viewing of CT scans. The methods do not require the use of an external calibration phantom; they are patient-specific in that the resulting calibration depends on measurements of gray-scale attenuation data (referred to herein as the HU-values) in the patient's CT scan; they can be used retrospectively on previously acquired scans or prospectively on new scans; and in some applications they can also be used on scans containing intravenous contrast. Because the methods facilitate automation, they are easily implemented clinically and are highly repeatable.

The overall phantomless calibration process 100 (in FIG. 1) is a computer-implemented method consisting of the following three general steps for calibrating a patient's CT scan 101, the results of which are saved to a computer or digital medium 105:
 a) Step 102: measure HU-values of one or more internal reference tissues in said CT scan (as well as air in some embodiments);
 b) Step 103: specify a quantitative calibration-information characterization. This is quantitative information that is specific to the scan being analyzed and that is eventually coupled with the HU-measurements from step 102 for the purposes of providing a patient-specific calibration. This step comprises sub-steps 130, 136, and optional step 135; and
 c) Step 104: calibrate the HU-values for a region of interest in the scan, using the measured measure HU-values of the internal reference tissues and the quantitative calibration-information characterization. This step comprises sub-steps 140, 150, and optional step 155.

The specifics of these general steps depend on the desired application and can be implemented in various different ways, depending on what type of internal reference tissue is used, the specifics of the sub-steps including what type of quantitative calibration-information characterization is used, whether or not optional steps 135 and 155 are employed, and the nature of the outcome measures produced by the overall calibration process. Step 102 can measure HU-values for different types of reference tissues, and this information is always used in step 104 and optionally in step 103. Sub-steps 130, 135, and 136, and sub-steps 140, 150, and 155 can each be implemented in different ways depending on the desired application. Different types of results can be produced by the calibration, depending on the application. For example, the main result could be a calibration equation, to be used in some later analysis, or, voxel-specific calibrated HU-values. The calibration equation and calibrated HU-values can be saved as various different outcomes, for example, a density or mass-fraction or porosity of a tissue of interest, or, can be saved as corrected HU-values (in Hounsfield Units), and results can be saved for different regions of interest, including different tissues of interest or the entire scan or portions of the scan. It should be clear to one of ordinary skill in the art from the foregoing and the following descriptions, that within the scope of this invention, general steps 102-104 can be performed in different ways, depending on the type of CT scan under analysis, anatomic site, tissue of interest, outcome of interest, level of desired automation, and the clinical application.

Two general embodiments for the phantomless calibration process 100 differ primarily in the type of quantitative calibration-information characterization used in general step 103. For the purposes of this invention, the term "quantitative calibration-information characterization" is defined as quantitative scan-specific information that specifies either the effective energy of the scan or values of an equivalent-density for one or more internal reference tissues, as well as air. Henceforth, these two general embodiments are referred herein as the "Effective-Energy" and the "Equivalent-Density" methods, respectively. For each method, various different specific embodiments are described below to convey the scope of the invention. For the Effective-Energy method, an estimate of effective energy of the patient's scan is used to assign known attenuation values to the chosen internal reference tissues. The original HU-values in the CT scan can be converted into "corrected" HU-values using this information, and can also be converted into measures of density, or equivalent, for a tissue of interest. This latter process utilizes a mixture-model of attenuation to appropriate the total energy-specific attenuation of any single voxel within the tissue of interest to a mass fraction-weighted summation of the energy-specific attenuations of specified mixture components (for example, bone and marrow). Once the mass fraction is thus calculated, a measure of density (or mass, porosity, or equivalent) of the mixture components can be calculated for the tissue of interest. For the Equivalent-Density method, instead of using the effective energy of the scan and known energy-specific attenuation values of the internal reference tissues as the basis for calibration, known values of an equivalent-density are assigned to the internal reference tissues; the major novelty of the Equivalent-Density method is its use of air and one of the internal reference materials, thus requiring only the processing of one internal reference tissue for its implementation.

In the Effective-Energy method, the quantitative calibration-information characterization comprises the known energy-specific mass-attenuation values of one or more internal reference tissues, optionally including air, which can be obtained from various prior-art data sources after estimating the effective energy of the patients' scan (typically in units of keV). Thus, in order to specify the quantitative calibration-information characterization for the Effective-Energy method, the effective energy of the scan must be estimated—which itself can be performed in a number of ways. One option is to base the estimate of effective energy empirically on scan-acquisition information (defined here as information on CT machine make and model, and/or information on the scan acquisition characteristics, such as peak tube potential); information could also be used on patient characteristics (body size, girth, body mass index). Any such empirical relations would be developed prior to the calibration process, and this option would not utilize any HU-values from the patient scan for the purposes of estimating the effective energy of the scan (but those HU-values would be used later in the calibration process). Another option is to base the estimate of effective energy on measured HU-values from one or more internal reference tissues in the scan and the known energy-attenuation relations for those tissues, optionally also using air. Some details of this option are described below. A third option is to use some type of prior-art or other energy-measuring hardware or software that is used with or otherwise integrated into the CT machine. For this option, the CT machine could be programmed to provide an estimate of the effective energy of the scan as part of the header information in the CT scan DICOM file, as input to the calibration process 100, to be used in sub-step 135. This option could therefore be considered under the umbrella of "scan-acquisition" information (sub-step 135).

One important feature of the Effective-Energy method is the use of an attenuation-based mixture model (sub-step 155) to map the total attenuation of a voxel in a region of interest in the CT scan to the calibrated outcome of clinical interest, the nature of which depends on the type of tissue of interest under analysis and the clinical application. For example, for bone applications, this outcome could be the bone density, or bone mineral density, or some equivalent measure of bone or mineral mass, content, porosity, or volume fraction; for liver applications, this outcome could be the fat content or fat fraction in the liver; for endocrine applications, this outcome could be the fat content or fat fraction in muscle; for coronary calcification applications, the outcome could be the volume of mineral in a blood vessel. In certain applications, the use of a mixture model 155 is important in order to provide correct calibrations across different scan-acquisition settings, particularly when the kVp is changed. This is because the attenuation characteristics of the real mixture components of various body tissues—for example solid bone and marrow/or fat in cancellous bone—change as the kVp (and effective energy of the scan) is changed, and unless a mixture model is used that properly accounts for such an energy-dependence of the attenuation characteristics of the real mixture components, errors will be introduced in the outcome measures of the overall calibration. Thus, another novel feature of this invention is the nature of the outcome of the calibration process, which can include measures of real tissue density and porosity, not just measures based on the content of the calibration materials in an external calibration phantom.

In the Equivalent-Density method, the quantitative calibration-information characterization comprises the known values of equivalent-density for air and one or more internal reference tissues, all of which are known from previous measurements, and which can be tabulated as a function of various scanner and patient factors. The novelty over any prior-art methods of phantomless calibration that require the use of equivalent-density values for two internal reference tissues—for example, Gudmundsdottir (1993), Pickhardt (2011)—is that the Equivalent-Density method requires the use of equivalent-density values for only one internal reference tissue since air is used to provide a second calibration point (although more than one internal tissue can optionally be used with air for this general embodiment). In the context of quantitative CT, the prior-art general term "equivalent-density" is typically used to refer to a calibrated value of density of a tissue of interest, or other region of interest in a CT scan, such that the attenuation observed for the tissue of interest equals the attenuation that would be expected for that value of concentration (or density) of an assumed mixture—typically the solution of mineral and water that is used in an external calibration phantom. For example, if an observed grayscale for a voxel of cancellous bone were 100 HU, and it turns out that a grayscale value of 100 HU would also occur for a 0.35 g/cm$^3$ mixture of a specified type of mineral-water solution, then the equivalent-density of the cancellous bone would be taken as 0.35 g/cm$^3$. Values of equivalent-density are limited in part because their units of measurement are tied to the specifics of the mixture materials in the external calibration used for their measurement. One further improvement over the prior art is the measurement of values of equivalent-density, using the Effective-Energy method, which enables values of equivalent-density for air and any internal tissues to be expressed in terms of units of solid bone and marrow (or fat and/or blood), or any other internal body tissues, none of which are specific to any type of external calibration phantom. For the Equivalent-Density method, the known values of equivalent-density are measured separately, before deployment of the Equivalent-Density method, and can be tabulated as a function of scan-acquisition data (scanner make and model, and various acquisition settings) and various patient factors; as noted, the Effective Energy method can be used for such measurements.

For both the Effective-Energy and Equivalent-Density methods, one key improvement over the prior art is the use of air to provide a second reference calibration point. Air is easily sampled from a CT scan and represents a robust and repeatable measure for the purposes of phantomless calibration. The use of air to provide a calibration point results in the need for just one internal reference tissue for the overall phantomless calibration. Compared to the prior-art methods, this novel feature facilitates implementation and automation since only one tissue needs to be identified in the scan and processed; and this feature also leads to greater precision and repeatability of the overall phantomless calibration. Furthermore, the need for processing of just a single internal reference tissue enables the phantomless calibration method to be applied to anatomic sites and applications for which it would be difficult or impossible to process two internal reference tissues. One example of such includes analysis at the proximal femur hip region, for which visceral fat is present but little other tissue is consistently available except for muscle, which, as discussed, is inherently limited for phantomless calibration because it represents a mixture of actual muscle and fat. Another example is the tibial or femoral diaphysis, for which air and dense cortical bone can be used as reference tissues, since again, no other suitable tissues are available (again, excluding muscle since it is typically mixed with an unknown amount of fat). Another example is the analysis of contrast-enhanced images, for which blood and muscle cannot be used as reference tissues since they are highly perfused by the contrast agent, whereas a large proportion of the fat remains relatively non-perfused. Thus, the use of air to provide a second calibration point in the current invention not only facilitates the use of phantomless calibration, but also enables its application to situations that would otherwise not be amenable to phantomless calibration methods that are based on analysis of two or more internal reference tissues.

In both the Effective-Energy and Equivalent-Density methods, different internal reference tissues can be used depending on the clinical application and site of measurement. Example tissues include blood tissue, visceral fat tissue, subcutaneous fat tissue, spleen tissue, spinal cord tissue, lean muscle tissue, and dense cortical bone tissue; fat tissue or dense cortical bone tissue is preferred in contrast-enhanced scans since these tissues are relatively non-perfused by typical contrast agents. This list of candidate internal reference tissues are recommended since they are relatively homogenous across patients and over time, and consist primarily of the parent tissue with only small added components of other tissues. For example, muscle tissue is not ideal for reference purposes since it typically contains a mixture of pure muscle tissue and fat tissue, the proportion of which can vary widely across individuals and over time; the same is true for marrow tissue. However, these tissues can work well if the fat content is known a priori to be very low and in that case the lean tissue can be considered to be pure with no fat content.

As depicted in FIG. 2, process 200 represents one general embodiment of the Effective-Energy method as applied to the measurement of a density of a tissue of interest in a patient's CT scan 101, many details of which are provided in subsequent paragraphs. In step 102, HU-values are measured from the scan for one internal reference tissue and for external air, the air serving as a second reference material. In general step 103, energy-specific values of attenuation are specified for said internal reference tissue and air. To do this, first, in sub-step 135, empirical relations are provided that relate certain scanner-acquisition information—for example, the scanner make and model, and the kVp value used in the scan acquisition—to effective energy of a scan. These relations are used to specify an effective energy of the patient's CT scan for their particular scanner-acquisition information. In sub-step 136, known values of attenuation as a function of effective energy are used to specify attenuation values as a function of effective energy for the internal reference tissue and air. In sub-step 130, information from sub-steps 135 and 136 is combined to provide energy-specific values of attenuation for the internal reference tissue and air for the estimated energy of the patient's CT scan. In general step 104, voxels in the tissue of interest in the scan are calibrated using the information provided by general step 103. To do this, in sub-step 140, a linear equation is developed between HU-value and attenuation, using the measured HU-values 102 and the energy-specific values of attenuation for the internal reference tissue and air 130. This equation can then be used for all voxels in the tissue of interest to map HU-values to attenuation values. In sub-step 155, a mixture-model for attenuation sharing is assumed for each voxel in the tissue of interest, in which the mass-attenuation of an individual voxel is assumed to be the mass-fraction-weighted sum of the mass-attenuations of each of the assumed components of the mixture (for which energy-specific values can also be obtained in sub-step 136). For a two-component mixture model, the only unknown is the mass-fraction of one of the components, which can be solved for, given the attenuation value for a voxel. In sub-step 150, these calculations are performed to provide as output a value of a measure of density for the tissue of interest based on the calculated value of mass-fraction. Any calibration results from sub-steps 140 or 150 can be saved on electronic media 105. This information can be used in any subsequent quantitative analysis of said tissue or scan or for any other purposes. This embodiment facilitates full automation since image processing of just a single internal reference tissue, for example, fat or blood or spinal cord, lends itself to automation, as does image processing of air, and no other user input is required.

As depicted in FIG. 3, process 300 represents another general embodiment of the Effective-Energy method as applied to the measurement of a density of a tissue of interest in a patient's CT scan 101. In this embodiment, the effective energy of the scan is estimated in sub-step 130 based on the measured HU-values 102 of two internal reference tissues and air and their known relations 136 between attenuation and effective energy; scanner-acquisition information in sub-step 135 is not utilized. In this embodiment, the specified value of effective energy is taken as the value that is most consistent with the observed HU-values in the scan. As applied to the internal reference tissues and air, this approach seeks to find an effective energy that provides the highest degree of correlation between the measured HU-values and the known values of attenuation—which depend on the effective energy—of the two internal reference tissues and air (in variations of this embodiment, three or more internal reference tissues can be used, with or without air). One method of finding this value is to iteratively assign values of effective energy, use statistical linear regression analysis to find an R2 value between the measured HU-values and the energy-specific attenuations values, and find the value of effective energy that produces the highest R2 value. Another method, which provides the same values of effective energy as the R2 method if just three materials are used for the latter, assumes a linear relation between HU-value and attenuation. Based on that linearity, one can equate various ratios of HU-values (HU) to corresponding ratios of energy-specific attenuation ($\mu$) for three reference materials, thereby finding the value of effective energy as the value providing equality in the following relation (in which the subscripts refer to the three reference materials: for example, 1=blood, 2=air, and 3=fat):

$$\frac{HU_1 - HU_2}{HU_1 - HU_3} = \frac{\mu_1 - \mu_2}{\mu_1 - \mu_3}$$

Compared to prior-art methods that have applied similar techniques using materials outside the body, such as using specialized calibration phantoms (Jacobson U.S. Pat. No. 4,788,706), the method used in this embodiment is novel for several reasons, including its use of air and internal reference tissues, therefore not requiring the use of any hardware. However, it should be clear to one of ordinary skill in the art, that any method of estimating effective energy of a scan can be used within the scope of this invention.

In all embodiments of the Effective-Energy method, the known values of attenuation as a function of effective energy provided in sub-step 136 for said internal reference tissues and air, and for any assumed mixture components in the mixture model in sub-step 155, can be obtained in a number of ways. For example, these values are documented in the ICRU tables (*Tissue Substitutes in Radiation Dosimetry and Measurement*, Report 44 of the International Commission on Radiation Units and Measurements, 1989, Bethesda, Md.; ISBN 0-913394-38-6). Another source is the XCOM program from the National Institute of Standards of Technology (XCOM: Photo Cross Sections Database, http://www.nist.gov/pml/data/xcom). It should be clear to one of ordinary skill in the art, that any source of such information can be used in sub-step 136 within the scope of this invention.

A number of different approaches can be used in sub-step 140 to map HU-values into energy-specific attenuation values. In one such method, a linear mapping is obtained between the energy-specific attenuation values 130 and HU-values 102 for the internal reference tissues. If only two internal reference tissues are used (or one internal reference tissue and air are used) for such purposes, a straight line fit can be calculated analytically. If three or more internal reference tissues are used—which can reduce measurement error due to poor signal-to-noise ratios in the reference materials—statistical approaches can be used for such purposes, for example, least-squares best-fit linear regression analysis. Note that different internal reference tissues can be used in Steps 103 and 104. For example, in process 300 (FIG. 3), the internal reference tissues used to estimate the energy of the scan in sub-step 130 do not have to be the same as the internal reference tissues used to form the relation in sub-step 140; preferably, if HU-values are measured for multiple internal reference tissues in step 102, air is used in 130 but not used in 140. Alternatively, if three or more internal reference tissues are used, a non-linear equation can be fit to the data in sub-step 140, although the relation between HU-values and attenuation is usually assumed to be linear in most CT scanners.

In sub-step 155, each voxel in the tissue of interest is assumed to be comprised of a mixture (e.g. the tissue of interest and some non-tissue component, for example, solid bone tissue and marrow or fat, when cancellous bone is the tissue of interest). The overall attenuation for the voxel is taken as the mass-fraction-weighted sum of attenuations of the mixture components, summed by their to-be-calculated mass fractions. When a two-component mixture is assumed for each voxel, the mass fraction of one tissue component can be directly solved for, since the mass fraction of the second component is equal to one minus the mass fraction of the first component. In that way, only one mass fraction is unknown and can be obtained for each voxel, and from that, a measure of density (or porosity or volume fraction, or equivalent) can be calculated for both components. It should be obvious to one of ordinary skill in the art that different types of density measures, or their equivalent, can be calculated as the output of interest depending on the tissue of interest or the application: apparent density, mineral density, volume fraction, porosity, mass fraction, or other equivalent measures pertaining to the amount of tissue of interest contained in each voxel. The known energy-specific attenuation properties of any mixture-component tissues (typically for bone applications: solid bone and fat, or solid bone and marrow, of solid bone and blood; or for liver applications: liver and fat) are also specified in sub-step 136, to be used in sub-step 150.

In another embodiment, instead of mapping the HU-values in each voxel to a measure of density of the underlying tissue of interest, instead a model 155 is assumed in which the HU-value of a voxel is attributed to the attenuation of some other type of mixture, in particular, a mixture of non-tissue components. For analysis of bone, for example, the HU-values can be calibrated in terms of a water solution of dipotassium phosphate ($K_2HPO_4$), or a water solution of calcium hydroxyapaptite ($Ca_{10}(PO_4)_6(OH)_2$), or a mixture of mineral and some type of either water-equivalent or marrow-equivalent or blood-equivalent material, in which the equivalence is based primarily on the attenuation characteristics. The calibrated HU-value for the tissue of interest is then expressed as an density of the assumed mixture based on an equivalence of attenuation: the voxel of the tissue of interest is assigned a density of the assumed mixture—the "equivalent-density"—so that the overall attenuation expected for that density value of the assumed mixture material equals the overall attenuation of the voxel of the tissue of interest. In this embodiment, the known attenuation characteristics of the mixture materials are also included in sub-step 136, to be used in sub-step 150.

In an application of the Effective-Energy method, it is used to measure values of equivalent-density for air and/or any reference tissues without the use of any external calibration phantom. In this application, referring to FIG. 3, scans for a plurality of patients are calibrated in terms of equivalent-density values but in which the tissues of interest for output purposes are taken as the air and any internal reference tissues. Using data collected from a plurality of patients, the resulting values of equivalent-density for the air and/or the internal reference tissues for the plurality of patients can be tabulated as a function of, or otherwise statistically or mathematically related to, various scanner, acquisition, and/or patient factors. The resulting dataset and information can then be used subsequently in various types of calibration methods for any new patients, including the Equivalent-Density calibration method. One improvement of this application of the Effective-Energy method over conventional methods is that an external calibration phantom does not need to be used to measure equivalent-density values for the air or any reference tissues; that is to say, this application enables values of equivalent-density for internal reference tissues to be measured from scans taken without the use of any external calibration phantom, and this can be performed retrospectively on already-taken scans or prospectively on new scans. It should be obvious to one of ordinary skill in the art that this particular application of the Effective-Energy method can be applied to measure equivalent-density values for the air or any reference tissues or any region of interest in a CT scan. Further, when using the Effective-Energy method, the equivalent-density outcome can represent a density of an assumed mixture comprised of tissue components (such as bone or fat), and is not restricted, as are the prior-art methods that use external phantoms to measure values of equivalent-density, to a density or concentration of an assumed mixture comprised of non-tissue components (such as water/plastic and mineral, as described in the previous paragraph). Further, the "density" measure, when using the Effective-Energy method, can be any quantitative measure describing the amount of tissue, for example but not limited to, a mass, a porosity, a volume fraction, or a mass fraction. In this way, the Effective-Energy method can be used to provide improved measures of effective-density for air and any internal reference tissues. One improvement over any prior-art methods of phantomless calibration that use measures of effective-density for an internal reference tissue is to utilize instead such improved measures of effective-density for the internal tissue.

In all these embodiments and applications, use of different internal reference tissues, depending on the anatomic site and clinical application, should be obvious to one of ordinary skill in the art for this method. For example, one could use fat tissue (visceral and/or subcutaneous), dense cortical bone tissue, blood tissue, spinal cord tissue, lean muscle tissue, liver tissue, spleen tissue, or urine contained within a bladder—all of which have relatively uniform attenuation characteristics across patients and over time. Also, instead of sampling air from outside of the body, one could also sample the HU-value of the air internal to the body (e.g. in the colon). In most circumstances, the HU-value of external air is approximately −1000 HU, and for cases in which the external air cannot be measured for some reason, this fixed HU-value for the air can be assumed. Utilizing a fixed value can be particularly useful in small field-of-view reconstructions, for which the external air is typically not visible. As noted above, the same tissues do not need to be used in Steps 103 and 104. Similarly, it should be obvious to one of ordinary skill in the art that one could use various different types of mixture models 155, depending on the tissue of interest and the clinical application. Further, the mixture model 155 does not have to exactly represent the tissue of interest (for example, a water-mineral solution can be assumed to represent real bone tissue; real bone can be modeled as a mixture of solid bone and blood, or solid bone and marrow, or solid bone and fat).

In CT scans that are not contrast-enhanced, the internal reference tissue is preferentially blood, spinal cord, spleen, fat, and/or dense cortical bone; in (intravenously) contrast-enhanced scans, the internal reference tissue is preferentially visceral fat, spinal cord, or dense cortical bone since the attenuation of these tissues are minimally affected by any perfusion of the contrast agents; in all cases air can also be used. For tissues of interest that are deeper within the body, visceral fat may be preferable over subcutaneous fat since visceral fat is typically deeper within the body and therefore is better positioned to reflect potential beam-hardening effects more locally to the tissue of interest.

In some applications of the Effective-Energy method, it is preferable to use dense cortical bone as the internal reference tissue. This embodiment can be particularly useful for analysis of bones that contain thick cortices, for example, analysis of the tibia, femur, or humerus, for which a portion of the diaphysis is present in the CT scan. Oftentimes in such situations, there is no alternative tissue available for a phantomless calibration—as noted above, muscle is difficult to process for phantomless calibration because it typically contains unknown amounts of fat tissue and thus the use of dense cortical bone (with air) enables a phantomless calibration to be performed. In this embodiment, an analysis of HU-values is first performed to identify a sub-region of the diaphyseal cortical bone in the scan that is not directly at the edge of the bone surface. The denser part of that bone is then assumed to comprise fully mineralized bone tissue, with an assumed low degree of vascular porosity (5-10%) and a known density of the solid bone tissue (a value of 2.05 g/cm$^3$, for example, is a reasonable estimate for fully mineralized human cortical bone tissue). Given the estimated effective energy of the scan, the measured HU-value of the air and of the denser part of the cortical bone are then related, respectively, to the assumed known attenuation of the air and the attenuation of fully mineralized bone tissue having such specified vascular porosity (filled with blood); in a simplified form of this analysis, one could neglect the vascular porosity.

It should be clear to one of ordinary skill in the art from the foregoing, that within the scope of this invention, general steps 102-104 can be performed and combined in different ways, depending on the anatomic site, tissue of interest, outcome of interest, level of desired automation, and the clinical application. As a result, the overall implementation of the Equivalent-Energy method can reflect different specifics for steps 102-104. For example, one implementation could measure HU-values in step 102 for internal reference tissues blood, fat, and spinal cord, use step 136 instead of step 135, and in step 155 use a mixture model of solid bone and marrow; another implementation could use all these parameters except in step 155 use a mixture model of liver and fat; another implementation could measure HU-values in step 102 for air and internal reference tissue blood, use step 135 instead of step 136, and in step 155 use a mixture model of solid bone and fat; yet another implementation could use all these parameters except in step 155 use a mixture model of mineral and water.

As depicted in FIG. 4, process 400 represents a general embodiment of the Equivalent-Density method as applied to the measurement of a density measure, or equivalent, of a tissue of interest in a patient's CT scan 101. The general steps are as follows: a) In step 102, HU-values are measured for air and for one or more internal reference tissues in the scan; b) In general step 103, known values are specified for the equivalent-density 130 of air and the internal reference tissues, which can be specified 135 based on scanner characteristics, scan acquisition settings, and/or patient factors; c) In general step 104, a relation 140 is developed between said HU-values and the known values of equivalent-density for air and internal reference tissues—typically using some type of mathematical equation, but alternatively a set of tabulated values or equivalent. This relation is then applied in step 150 to all voxels in the tissue of interest in order to map the HU-values for the tissue of interest into their respective values of equivalent-density. As with the Equivalent-Energy embodiments, the results of the calibration are saved on electronic media.

In the Equivalent-Density method, the known values of equivalent-density of air and the one or more internal reference tissues are measured and stored before clinical application. This method is particularly useful if only one internal reference tissue is used since that facilitates applications to many different anatomic sites and applications since oftentimes it is difficult or impossible to use multiple internal tissues for the purposes of calibration (due to problems such as contrast-agent perfusion, heterogeneity, or lack of availability). For more widespread validity of this calibration method, for example across different scanners, scanner acquisition settings, and for patients both large and small, the known equivalent-density values should be expressed in some relational form to these variable factors. Once developed and stored, these empirical relations can then be used in clinical practice for any new scan once these factors are specified for a specific patient scan; an external calibration phantom is not required. Regardless of how the values of the equivalent-density for the air and internal reference tissues are obtained a priori, the Equivalent-Density method is nevertheless patient-specific because it requires measurement of the HU-values of air and the internal reference tissue in order to calibrate the scan; compared to the prior art, it is unique because it exploits the use of air as a calibration point, enabling a scan to be calibrated by analyzing just a single internal reference tissue. The Equivalent-Density method, whether or not air is used as a reference material, is also unique when used with measures of equivalent-density that are derived from a mixture model comprised of tissue components (such solid bone and marrow/fat), as apposed to those in the prior art that are derived from a mixture model reflecting non-tissue components (such as mineral and water/plastic). Indeed, since any values of equivalent-density for reference materials that have been used so far in the prior art for phantomless calibration have always been expressed in terms of the density or concentration of non-tissue components—because the calibrations used to measure those values of equivalent-density have always been performed using an external calibration phantom—another improvement of the current invention over the prior art is the use of equivalent-density values that are expressed in terms of the density of tissue components. Such measures of equivalent-density, which can be provided by the Effective-Energy method, can then be used for one or more internal reference tissues in any form of phantomless calibration to overcome the limitations of expressing equivalent-density in terms of non-tissue components.

Once the scan is calibrated using either the Effective-Energy or Equivalent-Density methods, a quantitative analysis can subsequently be performed using the calibrated scan as input. Examples of such quantitative analyses include measuring properties of the tissue of interest, including an apparent density (in $mg/cm^3$), a mineral density (in $mg/cm^3$), an areal density (in $g/cm^2$), a volume (in $cm^3$), a volume fraction, a porosity, a mass (in g), or a mass fraction—these measures are referred to generically herein as "a density measure" or "a measure of density". Examples of tissues of clinical interest for quantitative analysis include bone, liver, muscle, brain white or gray matter, aortic mineral.

A variety of clinical CT scans can be calibrated according to the current invention, with or without intravenous contrast, including but not limited to abdominal, spine (lumbar, thoracic, or cervical), pelvic, and lung CT scans, scans for CT colonography and CT enterography, or CT angiography or CT calcium-scoring scans of the heart or abdomen. Calibration of the scan or body part or tissue or organ can be used to provide a quantitative measure of a tissue of interest; it can also be used to enhance the viewing and interpretation of CT scans, including further image processing. For example, segmentation routines can exploit a consistent calibration to provide images of body parts in CT scans that are more consistent across different settings and CT machines. Gray-scale levels can be automatically set based on calibrated values of the attenuation. For example, the output of step 140 in FIG. 1 can be used to convert HU-values in the original scan to true attenuation values or to corrected HU-values. Once the HU-values have been calibrated or corrected in a consistent manner in this way, fixed threshold values can be defined to optimize viewing of CT scans for specific clinical applications and those thresholds can lead to more consistent viewing across different scanners and patients and over time.

Any of the embodiments described herein may be used alone or together with one another in any combination. Inventions encompassed within this specification may also include embodiments that are only partially mentioned or alluded to or are not mentioned or alluded to at all in this brief summary or in the abstract. Although various embodiments of the invention may have been motivated by various deficiencies with the prior art, which may be discussed or alluded to in one or more places in the specification, the embodiments of the invention do not necessarily address any of these deficiencies. In other words, different embodiments of the invention may address different deficiencies that may be discussed in the specification. Some embodiments may only partially address some deficiencies or just one deficiency that may be discussed in the specification, and some embodiments may not address any of these deficiencies.

Other features, benefits, and advantages of the present invention will be apparent upon a review of the present disclosure, including the specification, drawings, and claims.

BRIEF DESCRIPTION OF THE DRAWINGS

The accompanying figures, in which like reference numerals refer to identical or functionally-similar elements throughout the separate views and which are incorporated in and form a part of the specification, further illustrate the present invention and, together with the detailed description of the invention, serve to explain the principles of the present invention.

DETAILED DESCRIPTION OF THE INVENTION

Figure 1:
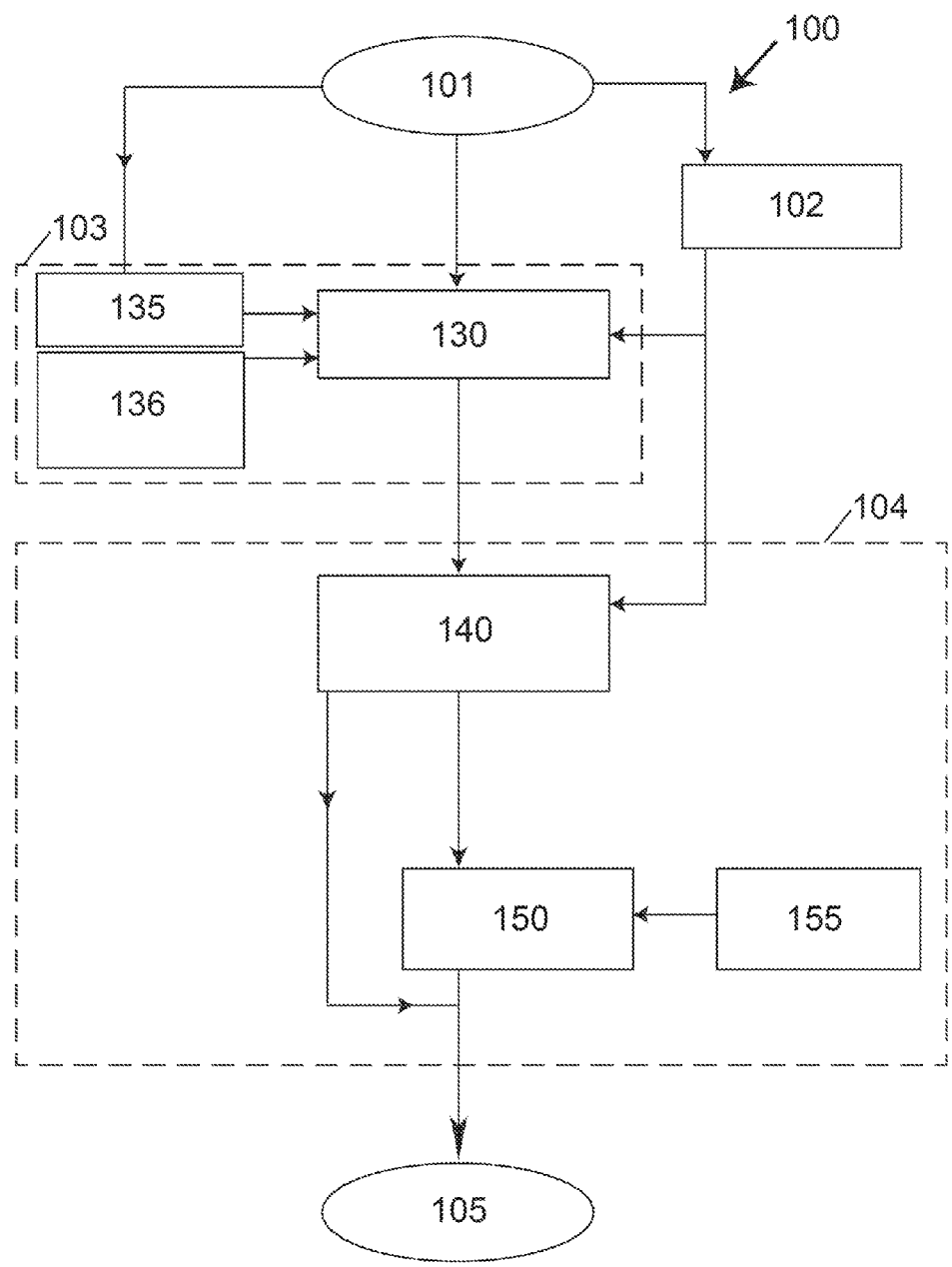
FIG. 1 illustrates a flowchart for overall process 100 of phantomless calibration of a patient's CT scan 101, in which general steps 102-104 are used to calibrate the scan in a patient-specific manner and save results to digital medium 105 (General step 103 comprises sub-steps 130, 135, and 136, and general step 104 comprises sub-steps 140, 150, and 155)/

Embodiments of the present invention provide a system and method for phantomless quantitative CT using the Effective-Energy and Equivalent-Density methods. The following description is presented to enable one of ordinary skill in the art to make and use the invention and is provided in the context of a patent application and its requirements.

Various modifications to the preferred embodiments and the generic principles and features described herein will be readily apparent to those skilled in the art. Thus, the present invention is not intended to be limited to the embodiments shown but is to be accorded the widest scope consistent with the principles and features described herein.

Definitions

The following definitions apply to some of the aspects described with respect to some embodiments of the invention. These definitions may likewise be expanded upon herein.

As used herein, the term "or" is generally intended to mean "and/or" unless otherwise indicated.

As used herein, the singular terms "a," "an," and "the" include plural referents unless the context clearly dictates otherwise. Thus, for example, reference to an object can include multiple objects unless the context clearly dictates otherwise.

Also, as used in the description herein and throughout the claims that follow, the meaning of "in" includes "in" and "on" unless the context clearly dictates otherwise.

As used herein, the term "set" refers to a collection of one or more objects. Thus, for example, a set of objects can include a single object or multiple objects. Objects of a set also can be referred to as members of the set. Objects of a set can be the same or different. In some instances, objects of a set can share one or more common properties.

As used herein, the term "adjacent" refers to being near or adjoining. Adjacent objects can be spaced apart from one another or can be in actual or direct contact with one another. In some instances, adjacent objects can be coupled to one another or can be formed integrally with one another.

As used herein, the terms "connect," "connected," and "connecting" refer to a direct attachment or link. Connected objects have no or no substantial intermediary object or set of objects, as the context indicates.

As used herein, the terms "couple," "coupled," and "coupling" refer to an operational connection or linking. Coupled objects can be directly connected to one another or can be indirectly connected to one another, such as via an intermediary set of objects.

As used herein, the terms "substantially" and "substantial" refer to a considerable degree or extent. When used in conjunction with an event or circumstance, the terms can refer to instances in which the event or circumstance occurs precisely as well as instances in which the event or circumstance occurs to a close approximation, such as accounting for typical tolerance levels or variability of the embodiments described herein.

As used herein, the terms "optional" and "optionally" mean that the subsequently described event or circumstance may or may not occur and that the description includes instances where the event or circumstance occurs and instances in which it does not.

As used herein, the term terms "HU-values", "CT numbers", "HU measurements" (or equivalent) should not be construed to be limiting only to the processing of CT scans in which the attenuation values of the image pixels or voxels are expressed as HU-values or Hounsfield Units. Instead, our use of the terms "HU-values", "HU measurements", "CT numbers" (or equivalent) should be interpreted more broadly to encompass any type of numerical values of the image pixels or voxels that are representative of X-ray attenuation. In particular, we use HU-values to mean the as-received grayscale values of the voxels in the CT scan. Ideally, these HU-values would be perfectly calibrated in terms of the attenuation of water and air, but in reality, due to various factors—such as degradation in hardware components in the CT scanner, electronic drift, or software or post-processing effects—the as-received grayscale values do need additional calibration, particularly if the scan data are to be used for subsequent quantitative analysis.

As used herein, the term "tissue" is used generally to mean some type of biological material contained within the body, either a hard (mineralized) tissue, soft (no mineral) tissue, or a fluidic tissue (for example, blood). Nevertheless, in that ordinary meaning of the term, "tissue" may still convey slightly different meanings depending on the context. It can refer to a bodily material of a single type, for example solid bone tissue, or it can sometimes refer to a more macro-level mixture of what is really multiple tissues, for example cancellous bone is really a mixture of solid bone tissue and marrow and blood and fat. Thus, "bone tissue" can be used to refer to solid bone or the mixture of bone and marrow/fat/blood. The latter mixture is sometimes referred to as an "organ" since the "tissue" is really composed of more than one type of tissue, but the term "tissue" may be used herein to refer to both tissue and organ meanings of the term. The proper meaning of the term "tissue" should therefore be obvious to one of ordinary skill in the art from the context and should not be afforded a more restrictive meaning if unclear from the context.

As used herein, the term "a measure of density" is used generally to mean any type of quantitative measure of a tissue or material, and not necessarily the density as strictly defined as the ratio of mass to volume. Examples include but are not limited to: a density, a concentration, a mass, a porosity, a volume fraction, and a mass fraction. The proper meaning of this term should therefore be obvious to one of ordinary skill in the art from the context and should not be afforded a more restrictive meaning if unclear from the context.

As used herein, the term "equivalent-density" is used to mean a measure of density assigned to a region of interest in a CT scan, such that the attenuation observed for that region of interest equals the attenuation that would be expected for that value of measure of density of an assumed mixture. The "equivalence" term denotes the equality of the attenuation between the region of interest and an assumed mixture having said value of equivalent-density. Thus, any value of equivalent-density depends on the nature of the assumed mixture in terms of the attenuation properties of its components. As noted in the previous definition, the "density" term is used broadly herein to mean any type of quantitative measure of a tissue or material. Thus, for example, the term equivalent-density can be used in some instances to mean equivalent-porosity, and the proper meaning should therefore be obvious to one of ordinary skill in the art from the context and should not be afforded a more restrictive meaning if unclear from the context.

The present invention may be applied to facilitate or even enable variety of clinical applications that would benefit from the use of quantitative CT, including but not limited to assessment of bone density and strength in osteoporosis applications; monitoring of osteoporosis drug treatments over time; pre-operative orthopaedic surgical planning for the hip, spine, or knee, including total joint replacement, spinal fusion, pedicle screw fixation, and fracture fixation of long bones; assessment of a degree of fracture healing or bone fusion; measurement of the amount of calcification in blood vessels or any soft tissues; measurement of fat content in the liver; and measurement of relative amounts of white and gray matter in the brain. Quantitative calibration of the attenuation values in a CT scan, with quantitative assessment of any particular tissue of interest, can also be used to improve and make more consistent the appearance and qualitative interpretation, and the quantitative analysis, of CT scans, by providing more consistent gray-scale values for different CT machines, different scanner settings, for different patients, and over time. In the following description, numerous specific details are set forth in order to provide a thorough understanding of the present invention. It will be apparent, however, to one skilled in the art, that the present invention may be practiced without some or all of these specified details and may be applied to any medical application in which a calibration would be beneficial. Well-known process steps of tissue quantification and image-processing have not been described in detail in order to not unnecessarily obscure the present invention.

FIG. 1 shows a flowchart of the overall process 100 of phantomless calibration, applicable to both the Effective-Energy and Equivalent-Density general embodiments. General descriptions of the invention have been described above. The following detailed descriptions are presented to further enable one of ordinary skill in the art to make and use the invention and to appreciate its variety of embodiments. Various modifications to the embodiments will be readily apparent to those skilled in the art, only some of which are depicted by the flowcharts in FIGS. 2-4 and the following embodiments. Thus, the present invention is not intended to be limited to the embodiments described here but is to be accorded the widest scope consistent with the principles and features described herein.

Figure 2:
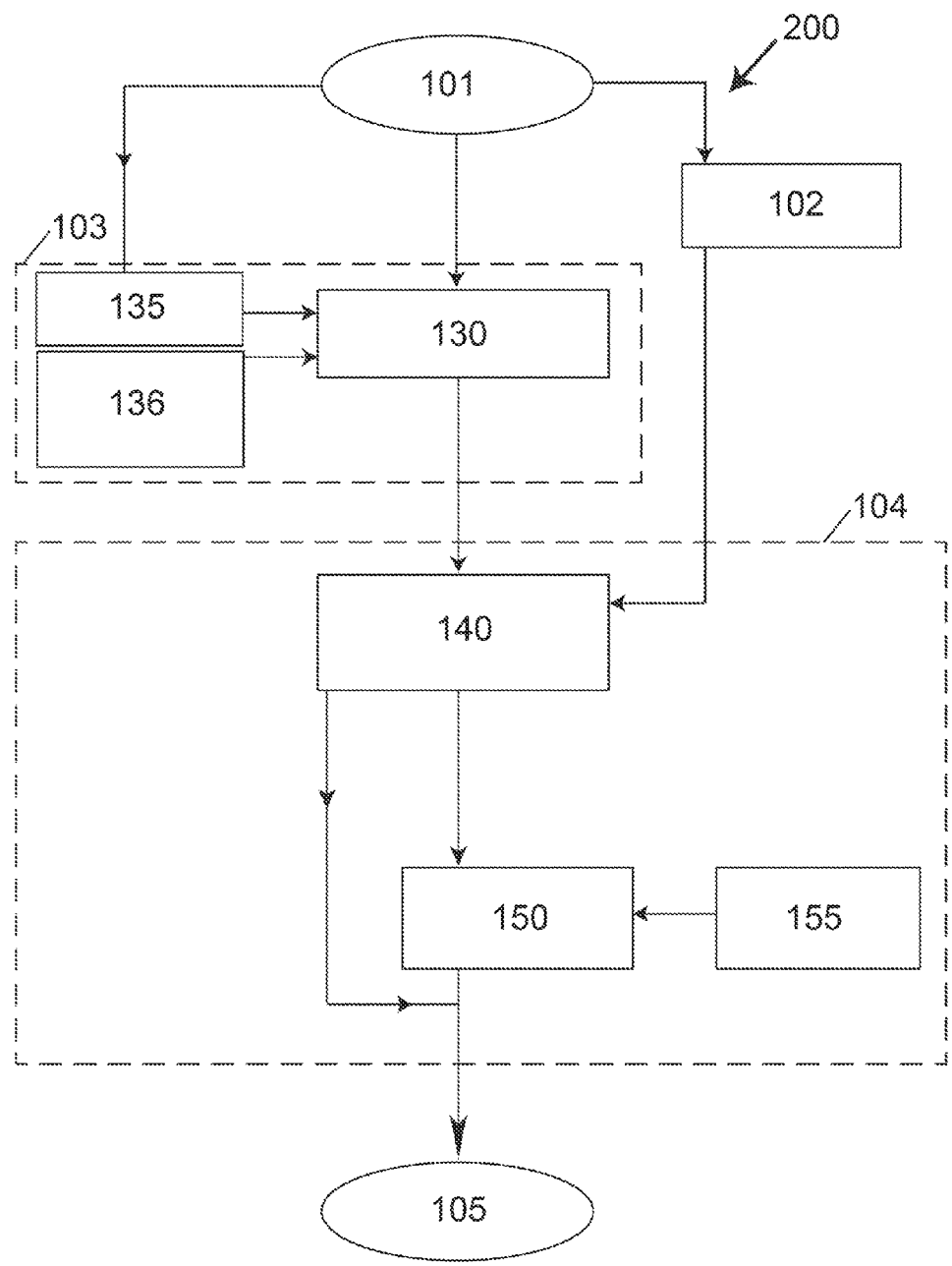
FIG. 2 illustrates a flowchart for overall process 200 of phantomless calibration of a patient's CT scan 101, using an Effective-Energy embodiment (In this embodiment, measurements from step 102 are used in step 104 but are not used in step 103)
Figure 3:
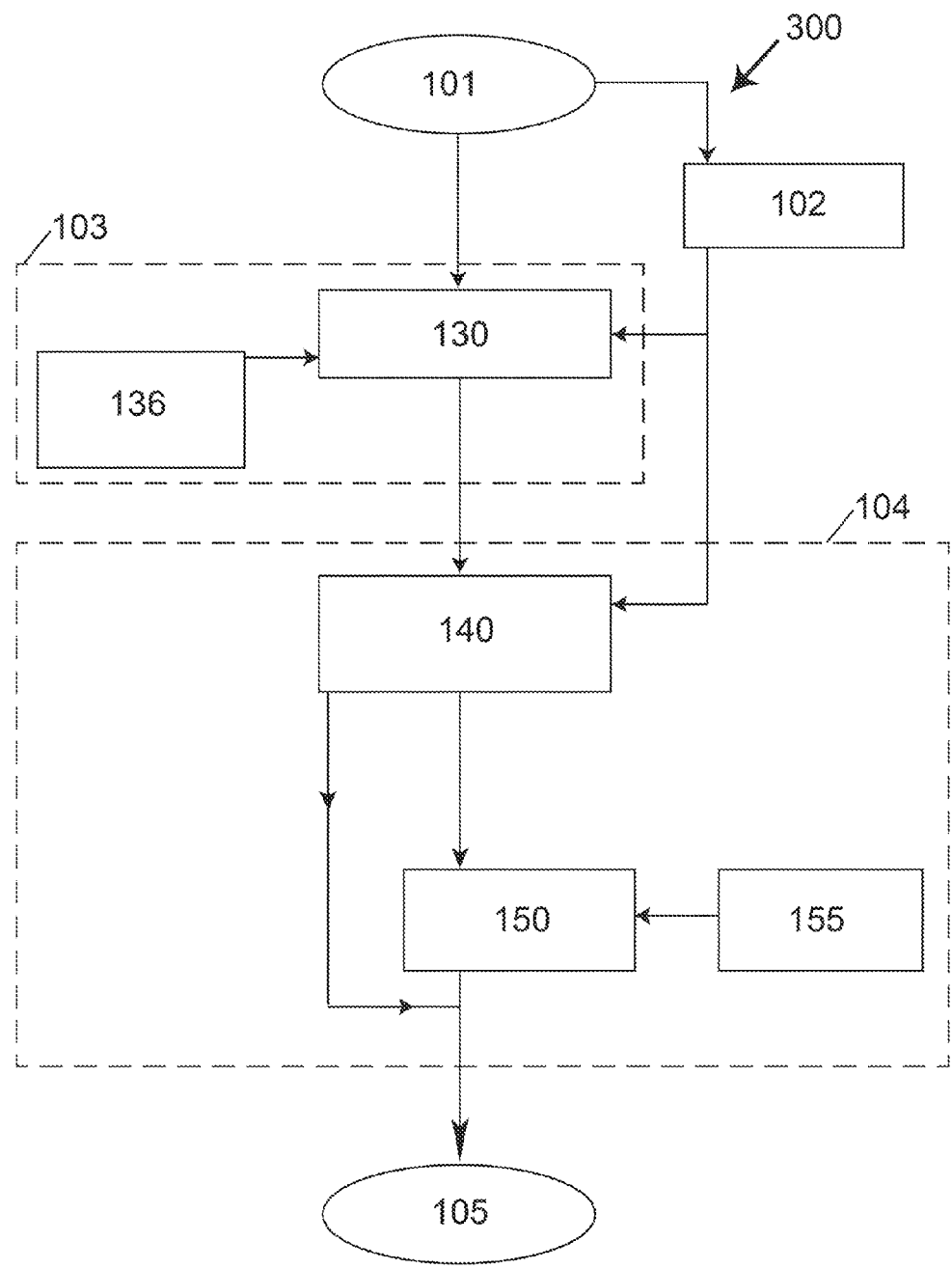
FIG. 3 illustrates a flowchart for overall process 300 of phantomless calibration of a patient's CT scan 101, using an Effective-Energy embodiment (In this embodiment, measurements from step 102 are used in both step 104 and step 103, and step 103 does not include sub-step 135)

In one specific embodiment of the Effective-Energy method, as depicted by the flowchart of overall process 200 in FIG. 2, the method is applied to provide calibrated measures of bone apparent density and bone volume fraction for cancellous bone, using as input a CT scan for a patient. Any type of CT scan can be used, so long as it contains the region of interest for the cancellous bone and is free from imaging artifacts, such as streaking from metal implants. Such image should also contain regions of one or more candidate internal reference tissues, and optionally air. The CT images could be generated by a traditional single-slice, helical, spiral, or multi-detector CT scanner, or, by portable or intra-operative C-Arm or O-Arm types of CT scanners, electron-beam CT scanners, or any type of CT scanner. Examples of specific types of CT exams include a hip or spine (lumbar and/or thoracic) CT, a pelvis CT, an abdominal CT, a cardiac CT, a CT scan of the femur, a CT scan of the lower leg including the knee joint, tibia and/or ankle joint; a CT scan performed for a virtual colonoscopy (so-called CT colonography), a CT enterography, a CT angiography, a calcium-scoring CT, and a lung CT. Scans can be with or without some type of contrast enhancement. No external calibration phantom is required. For this embodiment, the CT scan further contains the cancellous bone of interest, for example an elliptical-cylinder region-of-interest in the middle of a lumbar vertebral body, and perhaps other bones and organs. Any prior-art method used to scan patients and identify a region-of-interest for cancellous bone can be used, such as the methods reported by Cann (1987), Lenchik (2004), Hopper (2000), Pickhardt (2011), Mueller (2011), Miyabara (2012), all of which are incorporated herein by reference. HU-values in said region-of-interest of cancellous bone will be calibrated later in step 150.

Typically, the CT scan is stored and transferred between computers in DICOM file format and the grayscale values (or "CT numbers") are expressed within said digital file as HU-values. However, since the present invention does not require said grayscale values to be expressed as HU-values, the use of the terms "HU-values", "HU measurements" (or equivalent) in this invention should not be construed to limit the invention only to the processing of CT scans in which the grayscale values are expressed as HU-values and instead our use of the terms "HU-values", "HU measurements" or "CT numbers" (or equivalent) should be interpreted more broadly to encompass any grayscale values or units that are representative of X-ray attenuation. One exception to this more broad meaning is an embodiment in which a specific HU-value is assumed for the air for cases in which it is not possible or convenient to measure the HU-value of air from the patient's CT scan. For that specific embodiment, the grayscale values in the scan do indeed need to be expressed as HU-values, and an HU-value of −1000 is typically assumed for the air in that case, without actually making any measurement of HU-value for the air in the patient's scan.

In step 102 of overall process 200 in FIG. 2, HU-values are measured for one internal reference tissue, blood in this particular embodiment, and air, both from the patient's CT scan. The air can provide an important calibration point and its HU-value can be measured from the air in the scan either outside or inside (such as in the colon) the patient's body.

In step 103 of overall process 200 in FIG. 2, the effective energy of the scan (typically, in units of kiloelectron volts, keV) is estimated in sub-step 130 using the information contained in sub-step 135 on scanner and patient factors. In this embodiment, the effective energy for the patient's CT scan is estimated in sub-step 130 based on known empirical relations that relate the tube potential (in units of kVp) used for the patient's scan acquisition (information which is readily available in the DICOM header of the patient's scan) and the patient's body mass index (defined as the ratio of their mass or weight to the square of their height) to an estimate of the effective energy of the scan. These empirical relations, which are developed by measuring effective energy in a plurality of patients before any application of this embodiment, are provided in sub-step 130 for various makes and models of CT scanners, and can provide tabulated values of effective energy as a function of kVp and body mass index for the various makes and models of CT scanners.

In sub-step 136, known attenuation-energy relations are provided for air, the internal reference tissues, and the mixture-component tissues. These known relations can be obtained from a number of sources, all within the scope of this embodiment. For example, according to tabulated attenuation coefficients for various tissues in the ICRU tables—"*Tissue Substitutes in Radiation Dosimetry and Measurement*", Report 44 of the International Commission on Radiation Units and Measurements, Bethesda, Md., 1989; which is incorporated herein by reference—for an effective energy of 60 keV (or 0.06 MeV), the mass-attenuation coefficient ($\mu/\rho$, where $\mu$ is linear attenuation and p is density) is 0.0206 m$^2$/kg for blood and 0.0188 m$^2$/kg for air. Attenuation values are tabulated in that source for multiple values of effective energy, and for multiple tissues and materials. These tables, or equivalent prior-art sources, also provide attenuation-energy characteristics for the components of the mixture materials (to be used in sub-step 150). Other sources for this attenuation-energy information include the XCOM program from the National Institute of Standards of Technology (XCOM: Photo Cross Sections Database, http://www.nist.gov/pml/data/xcom). The information in sub-step 136 is not used to estimate the effective energy in this embodiment, although this information is used in sub-steps 140 and 150.

Having specified the effective energy of the patient's scan in step 103, in step 104 the measured HU-values of the air and blood from step 102 are related to their respective values of energy-specific attenuation using the information in sub-step 136. This enables one to analytically form a linear equation between HU-value (HU) and linear attenuation μ (in units of $cm^{-1}$) that can subsequently be used for any voxels in the patient's CT scan, including the cancellous bone:

$$\mu = aHU + b \quad (1)$$

in which a is the slope of the equation and b is the intercept. It is emphasized that the "HU-values" noted here are the grayscale numbers (or CT-numbers) as appearing for each voxel in the received CT scan for the patient. Using the measured HU-values for air and blood from step 102, and the two corresponding energy-specific values of linear attenuation obtained from sub-step 136, in sub-step 140 a linear equation between the two variables is formed, having slope a and intercept b as follows:

$$a = \frac{\mu_{air} - \mu_{blood}}{HU_{air} - HU_{blood}} \quad (2)$$

$$b = \mu_{air} - HU_{air}\left(\frac{\mu_{air} - \mu_{blood}}{HU_{air} - HU_{blood}}\right) \quad (3)$$

In sub-step 150 of overall process 200 in FIG. 2, the equation between HU-value and linear attenuation, obtained from step 104, is used to map HU-values to values of bone apparent density for all voxels in the cancellous bone of interest. In sub-step 155, a mixture model is assumed for the cancellous bone, specifically in this embodiment comprising a mixture of solid bone and yellow marrow components. Ideally, the components of the mixture should represent the real tissue of interest, especially in terms of matching the attenuation properties of the real components of the tissue of interest and how those attenuation properties depend on the effective energy of the scan. In the assumed mixture model, the mass-attenuation for a voxel is assumed to be the mass-fraction-weighted sum of the mass-attenuation of the mixture components, following known physical laws for X-ray attenuation in which the overall mass attenuation of a mixture is shared according to the mass fraction of the constituents of the mixture. For this embodiment, which is focused on calibration of cancellous bone, the non-bone component is assumed to be yellow marrow. But the choice of the non-bone component can depend on the type of bone (trabecular vs. cortical) or on specific clinical situation. For example, for cancellous bone, the fat content of marrow increases with age and thus in applications for older individuals, it can be beneficial instead to assume that the non-bone component of cancellous bone is fat, and indeed the use of fat as the non-bone mixture-component gives excellent performance when effective energy of the scan is varied via large changes in kVp. Thus, in sub-step 155 in process 200, for an assumed mixture comprising of solid bone and yellow marrow, the following equation can be used to describe the linear attenuation of each voxel of cancellous bone:

$$\mu = \rho_T \{m_b \mu_b/\rho_b + (1-m_b)\mu_m/\rho_m\} \quad (4)$$

in which μ is the overall linear attenuation of a voxel within a region of interest of cancellous bone in the CT scan, this attenuation being a linear function of the HU-value of that voxel in the CT scan as described in Equation (1) and in sub-step 140; $\rho_T$ is the overall or "apparent" density of that voxel (mass of all material in that voxel divided by the total volume of that voxel); $m_b$ is the unknown mass fraction of bone tissue in that voxel; $\mu_b$ is the known linear attenuation of solid bone tissue for a given scan energy (in $cm^{-1}$), $\rho_b$ is the known density of the solid bone tissue (in $g/cm^3$)—alternatively, $\mu_b/\rho_b$ is referred to as the mass attenuation of solid bone tissue, in units of $m^2/kg$, and is prescribed in sub-step 136; and $\mu_m/\rho_m$ is the known mass attenuation of yellow marrow (in units of $m^2/kg$) for a given scan energy, and is prescribed in sub-step 136.

Note that the $(1-m_b)$ term in this equation represents the mass fraction of the marrow, and can be expressed in terms of the mass fraction of the bone tissue since it is assumed that the mixture has only two attenuation-relevant components, namely, that the overall attenuation in each voxel is dominated by an attenuation due to the bone and the attenuation due to just one other non-bone tissue, namely the marrow in this example. Because of these assumptions, the only unknown in this equation is the mass fraction of the bone $m_b$ within the voxel, which is calculated as follows:

$$m_b = \frac{\mu - \mu_m}{\mu_b - \mu_m} \quad (5)$$

Once the mass fraction of bone $m_b$ is calculated for each voxel, in sub-step 150, values for the bone apparent density and bone volume fraction can be calculated. Bone apparent density (in units of $g/cm^3$) is calculated as the mass of actual bone tissue per voxel divided by the volume of that voxel, and a bone volume fraction is calculated as a volume of bone tissue per voxel divided by the total volume of that voxel (which is the ratio of the apparent to solid densities of the bone; or alternatively, 1-porosity). These calculations can be made if density values are assumed for solid bone tissue and solid marrow tissue. Thus, for example, the bone apparent density $\rho_{app-b}$ (in $g/cm^3$) and bone volume fraction $V_{f-b}$ are calculated from the mass fraction of bone $m_b$ using the following equations:

$$\rho_{app-b} = \frac{\rho_b m_b}{(1-m_b)\rho_b/\rho_m + m_b} \quad (6)$$

$$V_{f-b} = \rho_{app-b}/\rho_b = \frac{m_b}{(1-m_b)\rho_b/\rho_m + m_b} \quad (7)$$

These results are then saved on digital medium (105). Alternatively, an overall calibration equation is written to memory, relating the input HU-values to the output values of calibrated bone apparent density and bone volume fraction. This information can be used to perform a quantitative analysis of the bone at a later time. Examples of such quantitative analyses include measuring volumetric bone mineral density (in $mg/cm^3$), areal bone mineral density (in $g/cm^2$), bone volume fraction (or porosity), bone strength (in Newtons, N), bone stiffness (in N/m), mineral content (in g) or volume (in $mm^3$), or otherwise non-invasively assessing the biomechanical performance of a bone or bone-implant system.

Alternatively, an overall attenuation calibration equation, relating the input HU-values to the output linear attenuation values µ, is written to memory. This information can be used to perform a quantitative analysis of any tissue or organ at a later time by using a different mixture model appropriate for such tissue or organ. For example, for analysis of fat content in the liver, instead of assuming a voxel is composed of bone and marrow, one would assume that the voxel of interest in the liver is composed of liver and fat, and then use appropriate energy-specific values for the mass attenuation of solid liver and fat instead of solid bone and marrow. One could then solve for the mass fraction of fat in the liver, and from that calculate a volume fraction of fat or an apparent density of the fat or liver tissue. Thus, it should be clear to one of ordinary skill in the art that the method described in this embodiment, although described in detail for application to bone, can be applied to other tissues, and that different mixture models 155 can be applied to different tissues of interest in the same CT scan, but using the same equation 140 to convert HU-values to energy-specific attenuation values.

There are a number of additional variations that can be applied to this specific embodiment, all within the scope of process 200. Instead of using blood, depending on the anatomic site of interest and other clinical factors, one could use either fat tissue (visceral or subcutaneous), spinal cord tissue, spleen tissue, lean muscle tissue, liver tissue, dense cortical bone tissue, urine (contained within the bladder), or any other tissue within the body that is stable over time, relatively homogeneous in its composition, and is present in the CT scan in sufficient quantity and quality (no streaking artifacts or excessive noise, for example) to make a repeatable measurement of an HU-value. For example, spleen tissue can be used in some applications, for example, in liver applications. The use of spleen tissue in such an application is advantageous because the spleen is located relatively close to the liver, and thus any beam-hardening effects manifested in the liver would be manifested in a similar fashion in the adjacent spleen tissue and thus would be corrected by the calibration process. Use of fat is advantageous since in many patients it is present in large quantity and can easily be identified by image processing and therefore can provide a repeatable measurement that is easy to automate. Thus, it should be clear to one of ordinary skill in the art that the blood used in this embodiment can be substituted by another single tissue, depending on the particular application. In general, the HU-value measurements of the internal reference tissue and air can be obtained by a variety of image-processing methods known to one of ordinary skill in the art of image-processing, such as by placing regions of interest, applying region-growing algorithms, thresholding, performing a histogram analysis, using deformable-registration and/or computer-vision algorithms with or without a statistical atlas, or any combination thereof.

Since the availability and clarity of internal reference tissues can vary across people and across scan protocols and across different clinical applications, it should be clear to one of ordinary skill of the art that, within the scope of this invention, different internal reference tissues may be appropriate for different situations. For example, there may be local streaking or shading artifacts going through a potential internal reference tissue. In that event, a different internal reference tissue would likely provide a better calibration. Quantitative analysis of the histogram of HU-values in an internal reference tissue can be used to detect the presence of such artifacts. For example, if the mean HU-value of a preferred internal reference tissue falls outside an expected range of typical values (e.g. the mean HU-value for visceral fat is usually in the range of −60 to −100 HU), a different internal reference tissue can be selected for use. Alternatively, some measure of internal variation of HU-values of the reference tissue (for example, the standard deviation of values) may be considered too high, for example, due to highly localized streaking artifacts within the tissue. If it is deemed that any such artifacts would compromise the calibration, then a different internal reference tissue can be selected for use. Such a hierarchal approach based on a quantitative analysis of HU-values of the internal tissue can be used to provide a more robust calibration, which facilitates full automation of the overall calibration process.

Proper choice of the internal reference tissue also enables calibration of contrast-enhanced scans, for example, a CT enterography scan. In such scans, the HU-values of highly vascularized tissues (for example, blood and muscle) are increased (i.e. appearing brighter in intensity). Such contrast-enhanced tissues cannot be used as internal reference tissues for calibration since their HU-values no longer reflect the attenuation of the reference tissue itself, but also include the attenuation of the perfused contrast agent, which typically is of unknown concentration within the reference tissue. However, tissues with smaller blood vessels, such as visceral and subcutaneous fat, are much less affected by intravenous contrast and therefore can be used as internal reference tissues in contrast-enhanced scans. Dense cortical bone is also suitable as an internal reference tissue in contrast-enhanced scans since, even though the blood in the vascular pores does contain contrast, the low porosity of dense cortical bone and the high attenuation of solid bone tissue relative to the blood together result in an overall attenuation of the dense cortical bone that is relatively insensitive to the presence of the contrast agent in the blood.

In some situations, the HU-value for air can be pre-assigned if it is not easily measured from the scan since the HU-value of external air typically does not vary much across patients. In such cases, HU=−1000 is a recommended as a pre-assigned HU-value, although different pre-assigned HU-values may be used depending on the type of CT scanner and/or acquisition settings. Using a pre-assigned HU-value for air is useful in small-field-of-view scans, for which external air is often not visible and, depending on the region of the skeleton under analysis (e.g. the tibial diaphysis), there may also be no internal air visible either. Thus, air can still be used as reference material for the purposes of calibration, even if the HU-value of air is not measured for a patient and instead a pre-assigned HU-value is used. The calibration is still patient-specific since the internal reference tissue provides a patient-specific measurement of an HU-value for a reference tissue.

In the general, other scan acquisition data within the DICOM header could be contained in step 135 and used in step 130, such as excitation voltage, the x-ray source and any filtration, peak and minimum voltage, anode material, anode angle, filter material, and filter thickness, all of which can be used to calculate an effective energy of the patient's scan. Various methods exist in the prior art for such calculations, any of which can be used. For example, a CT scanner may make its own calculation of the effective energy of the scan, and write this information into the header fields of the DICOM file, information that can be obtained in sub-step 135. Or some external hardware device could be used to provide such information into sub-step 135.

Also in sub-step 135, additional patient physique information such as body size, weight, or girth might also be included and used to estimate the effective energy of the scan. An alternative, less detailed but still reliable approach, is to assign an effective energy to the scan based just on the value of kVp for the scan, without any patient-factor information, or to additionally develop relations that depend also on the make and model of the CT scanner. Alternatively, one could assign a generic value of effective energy to the scan based on limited scan information. For example, one could assign an effective energy value of 60 keV to the scan, which is a typical scan energy for 120 kVp scans, and use this for all patients scanned at that or similar settings (±20 kVp). This simple approach, while only approximate, can be useful in providing an approximate but highly consistent and automated calibration for a scan taken at 120 kVp or similar settings (which is currently the most common setting in clinical use).

In another variation, more than one internal reference tissue can be used in steps 102 and 104, for example, blood, fat, and spinal cord, and air is not included. In that event, in sub-step 140 one could use some form of statistical regression analysis (for example, least-squares best fit, linear or non-linear) between the values of HU-value and linear attenuation for the blood, fat, and spinal cord to obtain an equation between HU and attenuation. This equation could be linear or non-linear in form, depending on the degree of linearity in the observed relation (typically, any non-linearity is small and thus can usually be ignored). It should be clear to one of ordinary skill in the art that such an approach using multiple internal reference tissues could also use other tissues with, or instead of, blood, fat, and spinal cord—for example, dense cortical bone, spleen—and could include air.

In sub-step 155, depending on the application of process 200, different types of bone mixtures can be assumed for different anatomic sites, different types of bone, and for different patient factors (for example, age and sex). In older individuals, most of the marrow is often converted to fat, and one can assume the bone is a mixture of solid bone tissue and fat; this approach works well for analysis of vertebral trabecular bone, which is highly porous and has a large fat component. For bone tissue in general, one might use different mixture-models for cortical and cancellous bone. For cortical bone, for example, the marrow terms could be replaced by corresponding blood terms since blood primarily fills the (vascular) porosity in cortical bone. The distinction between cortical and trabecular bone is not well defined, but can be assumed to correspond to a bone volume fraction of about 0.85 (i.e. bone with a porosity of less than 15% can be assumed to be cortical bone). Thus, even at the same anatomic site for the same individual, different mixture equations could be applied to bone voxels, stratified by the bone volume fraction of the voxel for example, to distinguish between the different constituents of cortical and trabecular bone.

In sub-step 155, if the assumed mixture model for the cancellous bone is assumed to comprise more than one non-bone tissue, it is necessary to assume a fixed ratio between the multiple non-bone tissues, although that fixed ratio could be assumed to depend on patient factors, such as age and body-mass-index. The non-bone tissue could be assumed to comprise a combination of other tissues (e.g. red and yellow marrow) but with an assumed ratio of mass fractions between them. This ratio could be assumed to vary with patient factors (such as age and sex), but when solving for the mass fraction of bone, the ratio would be specified for a particular patient. Thus, in general, it is not necessary to assume only two tissue components in mixture model of sub-step 155, although for single-energy CT scans, there can only be one independent unknown mass-fraction term that can be solved for.

In general for any embodiments of this invention, while the flowcharts shown in FIGS. 1-4 depict a logical sequence of steps to implement the method of this invention, it should be clear to one of ordinary skill in the art that many of the equations, mathematical procedures, or computer coding of such can be mixed in order or combined in different ways to achieve the same results within the scope of this invention.

Figure 4:
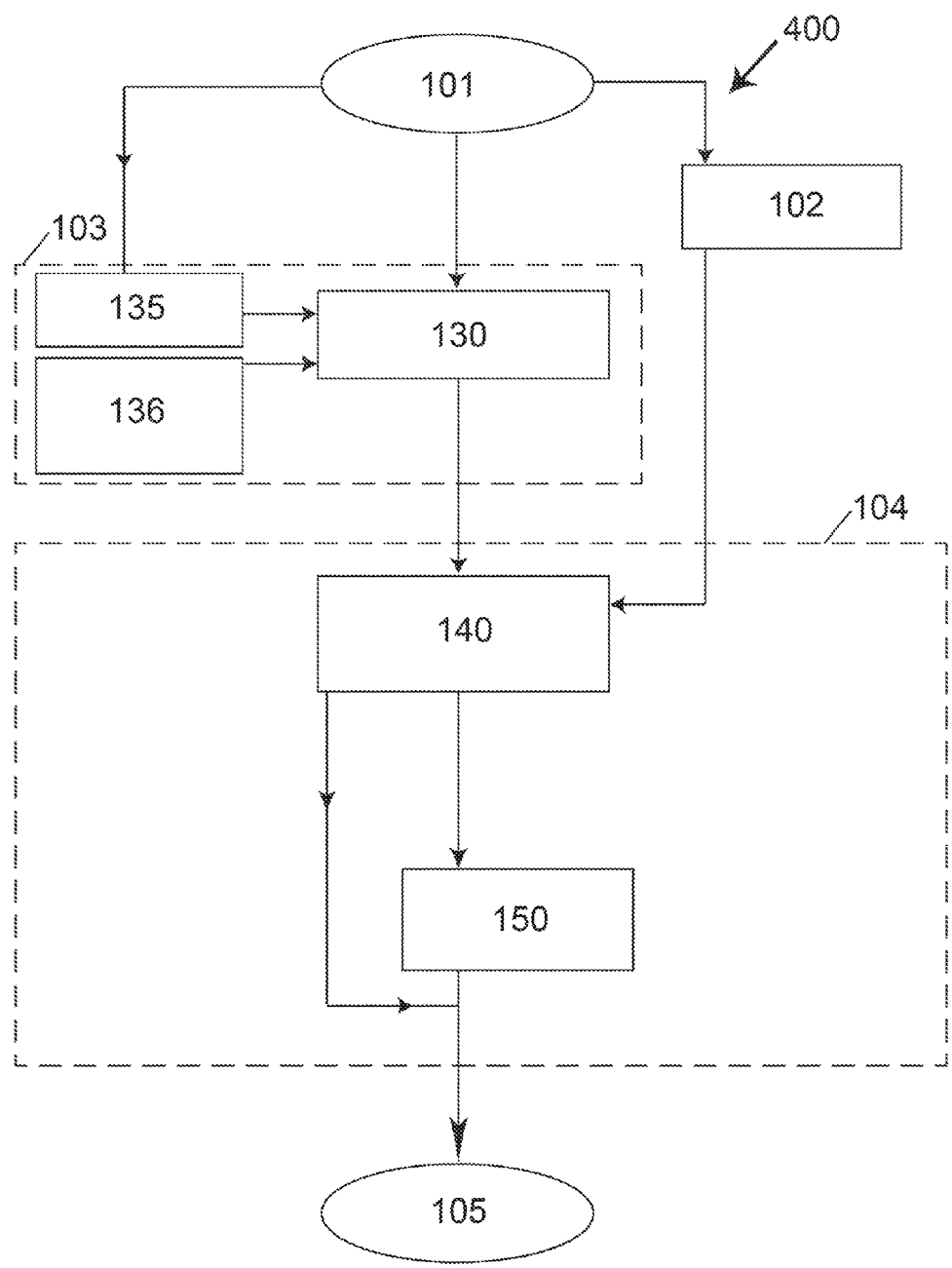
FIG. 4 illustrates a flowchart for overall process 400 of phantomless calibration of a patient's CT scan 101, using an Equivalent-Density embodiment (In this embodiment, measurements from step 102 are used in step 104 but are not used in step 103, and step 104 does not include sub-step 155).

In one specific embodiment of the Equivalent-Density method, as depicted by the flowchart of overall process 400 in FIG. 4, the method is applied using air and fat as reference materials, to provide calibrated measures of equivalent-density of a mixture of bone mineral and water, for the assessment of a region of cancellous bone in the human lumbar vertebral body. In the prior art, this type of outcome is commonly referred to as (volumetric) vertebral trabecular bone mineral density (BMD). The region of interest for the cancellous bone in the patient's CT scan 101 is specified, using prior-art methods as described for the previous embodiment. In step 102, HU-values are measured from scan 101 for visceral fat and external air. In sub-step 135, values for the kVp of the scan, and the scanner make and model are obtained. In sub-step 136, values of equivalent-density for the visceral and air are obtained, which are provided as a function of the scanner and patient factors as specified in sub-step 135. For this embodiment, these values of equivalent-density are expressed in terms of the concentration of a water solution of dipotassium phosphate (in $mg/cm^3$). These values may come from various sources, and all such information in sub-step 136 must be known prior to the application of this embodiment. This information can be obtained, for example, by measuring values of equivalent-density for fat and air in a plurality of patients, acquired using various scanner factors and for a wide range of patients, and using statistical analysis to formulate relations. The Equivalent-Energy method can be used for such measurements, thus not requiring the use of any external calibration phantom.

In sub-step 140, the HU-values of the air and fat are related to their respective equivalent-density values thus forming a linear equation between HU-value (HU) and equivalent-density (eDensity):

$$eDensity = cHU + d \quad (8)$$

in which c is the slope of this equation and d is the intercept, which are calculated as:

$$c = \frac{eDensity_{air} - eDensity_{fat}}{HU_{air} - HU_{fat}} \quad (9)$$

$$d = eDensity_{air} - HU_{air}\left(\frac{eDensity_{air} - eDensity_{fat}}{HU_{air} - HU_{fat}}\right) \quad (10)$$

In sub-step 150, this linear equation is then used to map HU-values to equivalent-density values for all voxels of interest in the cancellous bone. This result, when the values of equivalent-density are averaged overall all voxels in the cancellous bone of interest, is the desired output measure of vertebral trabecular BMD for the patient. It should be obvious to one of ordinary skill in the art that most of the variations discussed above for implementation of the embodiments for the Effective-Energy method also apply to this embodiment.

All these embodiments can be applied to a number of different clinical applications. In an example of overall process 400 as applied to a CT colonography exam, HU-values for blood from the abdominal aorta and air from the external air are measured. These HU-values, paired with their equivalent-density values are used to calibrate the trabecular bone of an L1 vertebral body.

In an example of overall process 400 as applied to a CT enterography exam, which typically has intravenous contrast, the HU-values for visceral fat in the hip region and air are measured. Note that fat is preferred over blood since the presence of contrast in blood confounds the attenuation of the blood. These HU-values, paired with their equivalent-density values are used to calibrate all bone in the proximal femur, and from them provide a measure of femoral neck areal BMD for the hip.

In an application of the Effective-Energy method, it can be used to provide "corrected" HU-values for a scan, which can be then subsequently processed for various other purposes. In such an embodiment, sub-step 155 is not performed, and instead "corrected" HU-values (calculated in sub-step 150) are produced as the main output. In this embodiment, the linear equation 140 mapping HU-values to energy-specific linear attenuation values is applied to all of the voxels in a region of interest in the CT scan (typically the entire CT scan). The resulting linear attenuation values ($\mu$) for all such voxels are then further processed to provide "corrected" HU-values for each voxel (HU*), according to the following known formula, which generally defines the Hounsfield Unit of a voxel in terms its (energy-specific) linear attenuation $\mu$ and the (energy-specific) linear attenuation of water $\mu_w$ (which can be specified using information in sub-step 136):

$$HU^* = 1000\left(\frac{\mu - \mu_w}{\mu_w}\right) \qquad (11)$$

Such "corrected" HU-values can be used subsequently as a basis for calibration of any tissues within the scan, or for improved viewing purposes of the scan by way of providing more consistent HU-values across patients, scanners, scan acquisition protocols, and over time. In one related application, HU-values first produced by the CT scanner are corrected according to this embodiment and the CT scan is overwritten or otherwise appended with the "corrected" HU-values for all voxels in the image, to be used for improved viewing and qualitatively interpreting of the scan. In another application of this embodiment, such corrected HU-values can be used to provide more consistent and improved HU-values for making quantitative estimates of a mass or density of various tissues. For that application, various prior-art methods of quantitatively measuring (uncorrected) HU-values for various types of tissue of interest are known, for example, Speliotes (2008) for liver, Pickhardt (2011) for bone, and Metter (2011) for brain, and are incorporated herein by reference.

In another clinical application of the Effective-Energy method, it is used to measure coronary calcification. Current prior-art methods for assessing calcium in the coronary artery result in an "Agatston score." This calcium score is generated for each CT cross-section by first multiplying a weighting value (based on the maximum observed uncalibrated HU-value in the artery) by the area of the calcification (in mm2) as observed in that CT cross-section. The sum of all calcium scores from the relevant CT cross-sections provides a total coronary calcium score, or the Agatston score. The Effective-Energy method provides an improvement over this prior-art by providing corrected and thus more consistent HU-values for measurement of an Agatston score. In a further improvement, the CT scan is calibrated according to the process 200 or 300, and in sub-step 155 all voxels in a region of interest in the calcified artery are assumed to comprise a tissue-component mixture of blood and calcium mineral. This enables HU-values of the artery to be calibrated in terms of a total mass of the calcium in the artery. This sort of outcome is more generalizable and easy to interpret than an Agatston score.

In another clinical application of the Effective-Energy method, it is used to measure the fat content of the liver, in an assessment of fatty liver disease. Current prior-art methods use single-energy-CT to assess the amount of fat in the liver by either directly sampling the hepatic uncalibrated HU-values from the liver, or, by comparing hepatic uncalibrated HU-values with splenic uncalibrated HU-values (from the spleen) by taking a ratio or difference of the two. In some cases, an external calibration phantom is used to calibrate the CT scans. In an improvement over the prior art, the Effective-Energy method is applied using processes 200 or 300 to provide a phantomless calibration, and further by assuming in sub-step 155 that the fatty liver is comprised of a liver-fat mixture, it can provide an outcome measure of fat fraction (fat mass divided by liver mass) or fat content (mass of fat) in the liver. The region of interest for the liver can either be sampled from simple circular regions of interest, or from the entire liver using advanced imaging processing methods (taking care to avoid large vessels and biliary structures). Alternatively, more consistent HU-values can be analyzed, as per the prior-art, but improved by the application of the Effective-Energy method to provide corrected HU-values, as described above.

In another clinical application of the Effective-Energy method, it is used to quantitatively evaluate brain edema. Prior-art methods quantify a ratio of HU-value in the gray matter to an HU-value in the white matter, all uncalibrated HU-values, and then compare the ratio to a specific clinical threshold for diagnostic purposes. Since the HU-values are uncalibrated, even their ratio can be confounded by factors that influence the depiction of the gray-scale HU-value. Such prior-art methods can be improved upon by the application of the Effective-Energy method to provide corrected HU-values, as described above. Furthermore, since the linear attenuation for gray matter and white matter vary as a function of effective energy, so too does their ratio. As a result, comparison of the ratio to a fixed threshold would not be appropriate for scans acquired at an energy that is different than the energy used to determine the fixed threshold. Therefore, a further improvement on the prior art is to apply the Effective-Energy method to provide a volume fraction each for "pure" gray and white matter from their respective cerebral regions, and then taking the ratio of these volume fractions.

A set of references have been discussed and provide background matter for the present invention, all expressly incorporated in their entireties for all purposes, are fully specified herein: 1. Agatston, A. S., W. R. Janowitz, F. J. Hildner, N. R. Zusmer, M. Viamonte, Jr., and R. Detrano, Quantification of coronary artery calcium using ultrafast computed tomography. J Am Coll Cardiol, 1990. 15(4): p. 827-32; 2 Budoff, M. J., J. Takasu, R. Katz, S. Mao, D. M. Shavelle, K. D. O'Brien, R. S. Blumenthal, J. J. Carr, and R. Kronmal, Reproducibility of CT measurements of aortic valve calcification, mitral annulus calcification, and aortic wall calcification in the multi-ethnic study of atherosclerosis. Acad Radiol, 2006. 13(2): p. 166-72; 3. Hoffmann, U., T. J. Brady, and J. Muller, Cardiology patient page. Use of new imaging techniques to screen for coronary artery disease. Circulation, 2003. 108(8): p. e50-3; 4. Bauer, J. S., T. D. Henning, D. Mueller, Y. Lu, S. Majumdar, and T. M. Link, Volumetric quantitative CT of the spine and hip derived from contrast-enhanced MDCT: conversion factors. Am J Roentgenol, 2007. 188(5): p. 1294-301; 5. Faulkner, K. G., C. E. Cann, and B. H. Hasegawa, Effect of bone distribution on vertebral strength: assessment with patient-specific nonlinear finite element analysis. Radiology, 1991. 179(3): p. 669-74; 6. Orwoll, E. S., L. M. Marshall, C. M. Nielson, S. R. Cummings, J. Lapidus, J. A. Cauley, K. Ensrud, N. Lane, P. R. Hoffmann, D. L. Kopperdahl, and T. M. Keaveny, Finite element analysis of the proximal femur and hip fracture risk in older men. J Bone Miner Res, 2009. 24(3): p. 475-83; 7. Cann, C. E., Quantitative CT applications: comparisons of current scanners. Radiology, 1987. 162: p. 257-261; 8. Pickhardt, P. J., L. J. Lee, A. M. del Rio, T. Lauder, R. J. Bruce, R. M. Summers, B. D. Pooler, and N. Binkley, Simultaneous screening for osteoporosis at CT colonography: bone mineral density assessment using MDCT attenuation techniques compared with the DXA reference standard. J Bone Miner Res, 2011. 26(9): p. 2194-203; 9. Summers, R. M., N. Baecher, J. Yao, J. Liu, P. J. Pickhardt, J. R. Choi, and S. Hill, Feasibility of simultaneous computed tomographic colonography and fully automated bone mineral densitometry in a single examination. J Comput Assist Tomogr, 2011. 35(2): p. 212-6; 10. Boden, S. D., D. J. Goodenough, C. D. Stockham, E. Jacobs, T. Dina, and R. M. Allman, Precise measurement of vertebral bone density using computed tomography without the use of an external reference phantom. J Digit Imaging, 1989. 2(1): p. 31-8; 11. Gudmundsdottir, H., B. Jonsdottir, S. Kristinsson, A. Johannesson, D. Goodenough, and G. Sigurdsson, Vertebral bone density in Icelandic women using quantitative computed tomography without an external reference phantom. Osteoporos Int, 1993. 3(2): p. 84-9; 12. Tissue Substitutes in Radiation Dosimetry and Measurement, Report 44 of the International Commission on Radiation Units and Measurements. 1989, Bethesda, Md.; 13. Millner, M. R., W. H. Payne, R. G. Waggener, W. D. McDavid, M. J. Dennis, and V. J. Sank, Determination of effective energies in CT calibration. Medical Physics, 1978. 5(6): p. 543-5; 14. Tofts, P. S., Definitions of effective energy in computed tomography. Phys Med Biol, 1981. 26(2): p. 313-7; 15. Mueller, D. K., A. Kutscherenko, H. Bartel, A. Vlassenbroek, P. Ourednicek, and J. Erckenbrecht, Phantom-less QCT BMD system as screening tool for osteoporosis without additional radiation. Eur J Radiol, 2011. 79(3): p. 375-81; 16. Takikawa, S., V. Dhawan, P. Spetsieris, W. Robeson, T. Chaly, R. Dahl, D. Margouleff, and D. Eidelberg, Noninvasive quantitative fluorodeoxyglucose PET studies with an estimated input function derived from a population-based arterial blood curve. Radiology, 1993. 188(1): p. 131-6; 17. Aslam, R., J. Yee, A. Keedy, T. Joseph, and A. Chau. Assessment of bone mineral density on CT colonography. in SSG13-09 Proc 94th Scientific Assembly and Annual Meeting. 2008. Chicago: Radiological Society of North America; 18. Hopper, K. D., M. P. Wang, and A. R. Kunselman, The use of clinical CT for baseline bone density assessment. J Comput Assist Tomogr, 2000. 24(6): p. 896-9; 19. Miyabara, Y., D. Holmes, 3rd, J. Camp, V. M. Miller, and A. E. Kearns, Comparison of calibrated and uncalibrated bone mineral density by CT to DEXA in menopausal women. Climacteric, 2012. 15(4): p. 374-81; 20. Norton, M. R. and C. Gamble, Bone classification: an objective scale of bone density using the computerized tomography scan. Clin Oral Implants Res, 2001. 12(1): p. 79-84; 21. Toussaint, N. D., K. K. Lau, B. J. Strauss, K. R. Polkinghorne, and P. G. Kerr, Using vertebral bone densitometry to determine aortic calcification in patients with chronic kidney disease. Nephrology (Carlton), 2010. 15(5): p. 575-83; 22. Augustine, K., J. Camp, D. Holmes, P. Huddleston, L. Lu, M. Yaszemski, and R. Robb, Fracture risk assessment: improved evaluation of vertebral integrity among metastatic cancer patients to aid in surgical decision-making. SPIE Proceedings, 2012. 8317; 23. Bauer, J. S., S. Virmani, and D. K. Mueller, Quantitative CT to assess bone mineral density as a diagnostic tool for osteoporosis and related fractures, P. Healthcare, Editor 2010; 24. Lenchik, L., R. Shi, T. C. Register, S. R. Beck, C. D. Langefeld, and J. J. Carr, Measurement of trabecular bone mineral density in the thoracic spine using cardiac gated quantitative computed tomography. Journal of Computer Assisted Tomography, 2004. 28(1): p. 134-9; 25. McCullough, E. C., Photon attenuation in computed tomography. Med Phys, 1975. 2(6): p. 307-20; 26. Isherwood, I., R. A. Rutherford, B. R. Pullan, and P. H. Adams, Bone-mineral estimation by computer-assisted transverse axial tomography. Lancet, 1976. 2(7988): p. 712-5; 27. Goodsitt, M. M., Beam hardening errors in post-processing dual energy quantitative computed tomography. Med Phys, 1995. 22(7): p. 1039-47; 28. Mah, P., T. E. Reeves, and W. D. McDavid, Deriving Hounsfield units using grey levels in cone beam computed tomography. Dentomaxillofac Radiol, 2010. 39(6): p. 323-35; 29. Ma, X., N. S. Holalkere, R. A. Kambadakone, M. Mino-Kenudson, P. F. Hahn, and D. V. Sahani, Imaging-based quantification of hepatic fat: methods and clinical applications. Radiographics, 2009. 29(5): p. 1253-77; 30. Speliotes, E. K., J. M. Massaro, U. Hoffmann, M. C. Foster, D. V. Sahani, J. N. Hirschhorn, C. J. O'Donnell, and C. S. Fox, Liver fat is reproducibly measured using computed tomography in the Framingham Heart Study. J Gastroenterol Hepatol, 2008. 23(6): p. 894-9; 31. Metter, R. B., J. C. Rittenberger, F. X. Guyette, and C. W. Callaway, Association between a quantitative CT scan measure of brain edema and outcome after cardiac arrest. Resuscitation, 2011. 82(9): p. 1180-5; and 32. Crawley, E. O., W. D. Evans, and G. M. Owen, A theoretical analysis of the accuracy of single-energy CT bone-mineral measurements. Phys Med Biol, 1988. 33(10): p. 1113-27.

The methods may be implemented by a suitably programmed general-purpose computer system, such as by machine instructions embodied in appropriate computer readable media. For example, a computer system may function as a basic computer in implementing the present invention. The computer system includes a central processing unit (CPU), such as one of the PC microprocessors or workstations or other microprocessor or microcontroller or controller, is provided and interconnected to various other components by a system bus. An operating system runs on the CPU, and provides control and is used to coordinate the function of the various components of the system. The operating system may be one of the commercially available operating systems such as Microsoft's Windows, as well as workstation, UNIX and AIX operating systems, and the like. One or more application programs, controlled by the system, are moved into and out of a main memory RAM. These programs include the program of the present invention to be subsequently described in combination with local or wide-area network systems, such as for example, the Internet. A read only memory (ROM) is connected to the CPU via the bus and includes the Basic Input/Output System (BIOS) that controls the basic computer functions. The RAM, an I/O adapter and a communications adapter are also interconnected to the system bus. The I/O adapter may be a Small Computer System Interface (SCSI) adapter that communicates with a disk storage device. The Communications adapter interconnects the bus with an outside network enabling the data processing system to communicate with other such systems over a Local Area Network (LAN) or Wide Area Network (WAN), which includes, of course, the Internet, the WEB, intranets, extranets, and other public and private networks. The terms associated with the network are meant to be generally interchangeable and are so used in the present description of the distribution network. I/O devices are also connected to the system bus via a user interface adapter and a display adapter. A keyboard and a pointing device (e.g., a mouse) are all interconnected to the bus through the user interface adapter. The display adapter includes a frame buffer, which is a storage device that holds a representation of each pixel on a monitor or a display screen. Images may be stored in the frame buffer for display on the monitor through various components, such as a digital to analog converter and the like. By using the aforementioned I/O devices, a user is capable of inputting information to the system through the keyboard (or other input device) or mouse (or other pointing system) and receiving output information from the system via display. The system also contains a memory cache and includes a portion of a disk storage drive and a portion of RAM 125.

The system, method, and computer program product described in this application may, of course, be embodied in hardware; e.g., within or coupled to a Central Processing Unit ("CPU"), microprocessor, microcontroller, System on Chip ("SOC"), or any other programmable device. Additionally, the system, method, and computer program product may be embodied in software (e.g., computer readable code, program code, instructions and/or data disposed in any form, such as source, object or machine language) disposed, for example, in a computer usable (e.g., readable) medium configured to store the software. Such software enables the function, fabrication, modeling, simulation, description and/or testing of the apparatus and processes described herein. For example, this can be accomplished through the use of general programming languages (e.g., C, C++), GDSII databases, hardware description languages (HDL) including Verilog HDL, VHDL, AHDL (Altera HDL) and so on, or other available programs, databases, nanoprocessing, and/or circuit (i.e., schematic) capture tools. Such software can be disposed in any known computer usable medium including semiconductor, magnetic disk, optical disc (e.g., CD-ROM, DVD-ROM, etc.) and as a computer data signal embodied in a computer usable (e.g., readable) transmission medium (e.g., carrier wave or any other medium including digital, optical, or analog-based medium). As such, the software can be transmitted over communication networks including the Internet and intranets. A system, method, and computer program product embodied in software may be included in a semiconductor intellectual property core (e.g., embodied in HDL) and transformed to hardware in the production of integrated circuits. Additionally, a system, method, and computer program product as described herein may be embodied as a combination of hardware and software.

One of the preferred implementations of the present invention is as a routine in an operating system (e.g., a stored program computer including a computing device executing instructions accessed from a memory) made up of programming steps or instructions resident in a memory of a computing system as well known, during computer operations. Until required by the computer system, the program instructions may be stored in another readable medium, e.g. in a disk drive, or in a removable memory, such as an optical disk for use in a CD ROM computer input or in a floppy disk for use in a floppy disk drive computer input. Further, the program instructions may be stored in the memory of another computer prior to use in the system of the present invention and transmitted over a LAN or a WAN, such as the Internet, when required by the user of the present invention. One skilled in the art should appreciate that the processes controlling the present invention are capable of being distributed in the form of computer readable media in a variety of forms.

Any suitable programming language can be used to implement the routines of the present invention including C, C++, Java, assembly language, etc. Different programming techniques can be employed such as procedural or object oriented. The routines can execute on a single processing device or multiple processors. Although the steps, operations or computations may be presented in a specific order, this order may be changed in different embodiments. In some embodiments, multiple steps shown as sequential in this specification can be performed at the same time. The sequence of operations described herein can be interrupted, suspended, or otherwise controlled by another process, such as an operating system, kernel, and the like. The routines can operate in an operating system environment or as stand-alone routines occupying all, or a substantial part, of the system processing.

In the description herein, numerous specific details are provided, such as examples of components and/or methods, to provide a thorough understanding of embodiments of the present invention. One skilled in the relevant art will recognize, however, that embodiments of the invention can be practiced without one or more of the specific details, or with other apparatus, systems, assemblies, methods, components, materials, parts, and/or the like. In other instances, well-known structures, materials, or operations are not specifically shown or described in detail to avoid obscuring aspects of embodiments of the present invention.

A "computer-readable medium" for purposes of embodiments of the present invention may be any medium that can contain, store, communicate, propagate, or transport the program for use by or in connection with the instruction execution system, apparatus, system or device. The computer readable medium can be, by way of example only but not by limitation, an electronic, magnetic, optical, electromagnetic, infrared, or semiconductor system, apparatus, system, device, propagation medium, or computer memory.

A "processor" or "process" includes any human, hardware and/or software system, mechanism or component that processes data, signals or other information. A processor can include a system with a general-purpose central processing unit, multiple processing units, dedicated circuitry for achieving functionality, or other systems. Processing need not be limited to a geographic location, or have temporal limitations. For example, a processor can perform its functions in "real time," "offline," in a "batch mode," etc. Portions of processing can be performed at different times and at different locations, by different (or the same) processing systems.

Reference throughout this specification to "one embodiment", "an embodiment", or "a specific embodiment" means that a particular feature, structure, or characteristic described in connection with the embodiment is included in at least one embodiment of the present invention and not necessarily in all embodiments. Thus, respective appearances of the phrases "in one embodiment", "in an embodiment", or "in a specific embodiment" in various places throughout this specification are not necessarily referring to the same embodiment. Furthermore, the particular features, structures, or characteristics of any specific embodiment of the present invention may be combined in any suitable manner with one or more other embodiments. It is to be understood that other variations and modifications of the embodiments of the present invention described and illustrated herein are possible in light of the teachings herein and are to be considered as part of the spirit and scope of the present invention.

Embodiments of the invention may be implemented by using a programmed general purpose digital computer, by using application specific integrated circuits, programmable logic devices, field programmable gate arrays, optical, chemical, biological, quantum or nanoengineered systems, components and mechanisms may be used. In general, the functions of the present invention can be achieved by any means as is known in the art. Distributed, or networked systems, components and circuits can be used. Communication, or transfer, of data may be wired, wireless, or by any other means.

It will also be appreciated that one or more of the elements depicted in the drawings/figures can also be implemented in a more separated or integrated manner, or even removed or rendered as inoperable in certain cases, as is useful in accordance with a particular application. It is also within the spirit and scope of the present invention to implement a program or code that can be stored in a machine-readable medium to permit a computer to perform any of the methods described above.

Additionally, any signal arrows in the drawings/Figures should be considered only as exemplary, and not limiting, unless otherwise specifically noted. Furthermore, the term "or" as used herein is generally intended to mean "and/or" unless otherwise indicated. Combinations of components or steps will also be considered as being noted, where terminology is foreseen as rendering the ability to separate or combine is unclear.

The foregoing description of illustrated embodiments of the present invention, including what is described in the Abstract, is not intended to be exhaustive or to limit the invention to the precise forms disclosed herein. While specific embodiments of, and examples for, the invention are described herein for illustrative purposes only, various equivalent modifications are possible within the spirit and scope of the present invention, as those skilled in the relevant art will recognize and appreciate. As indicated, these modifications may be made to the present invention in light of the foregoing description of illustrated embodiments of the present invention and are to be included within the spirit and scope of the present invention.

Thus, while the present invention has been described herein with reference to particular embodiments thereof, a latitude of modification, various changes and substitutions are intended in the foregoing disclosures, and it will be appreciated that in some instances some features of embodiments of the invention will be employed without a corresponding use of other features without departing from the scope and spirit of the invention as set forth. Therefore, many modifications may be made to adapt a particular situation or material to the essential scope and spirit of the present invention. It is intended that the invention not be limited to the particular terms used in following claims and/or to the particular embodiment disclosed as the best mode contemplated for carrying out this invention, but that the invention will include any and all embodiments and equivalents falling within the scope of the appended claims. Thus, the scope of the invention is to be determined solely by the appended claims.

What is claimed as new and desired to be protected by Letters Patent of the United States is:

1. A computer-implemented method for measuring a calibrated value of an equivalent-density parameter for a region of interest in a CT scan of a patient, without the use of a calibration phantom, using a set of pre-determined values of said equivalent-density parameter for air and just one internal reference tissue, the method comprising the steps of:
    (a) specifying a pre-determined value of said equivalent-density parameter for said internal reference tissue;
    (b) specifying a pre-determined value of said equivalent-density parameter for air;
    (c) measuring from said CT scan an HU-value for said internal reference tissue;
    (d) measuring from said CT scan an HU-value for air;
    (e) using said measured HU-values and said specified pre-determined values of said equivalent-density parameter to convert the HU-values for said region of interest into values of said equivalent-density parameter.

2. The method of claim 1 wherein said equivalent-density parameter comprises one or more parameters selected from the group consisting of an equivalent-density, equivalent-mass, equivalent-volume, equivalent-porosity, equivalent-volume fraction, equivalent-mass fraction, equivalent-concentration, and combinations thereof.

3. The method of claim 1 wherein said internal reference tissue includes one tissue selected from the group consisting of blood, visceral fat, subcutaneous fat, spinal cord, lean muscle, dense cortical bone, liver, and spleen.

4. The method of claim 3 wherein said visceral fat is located near a vertebral body or a proximal femur, or said blood is located near a vertebral body.

5. The method of claim 1 wherein said pre-determined value of equivalent-density for said internal reference tissue or air is specified responsive to one or more parameters selected from the group consisting of a scanner, a scanner model, a scanner manufacturer, a scan-acquisition parameter, a patient factor, and combinations thereof.

6. The method of claim 1 wherein said value of said equivalent-density parameter for said internal reference tissue or air is specified responsive to a specified effective energy of said CT scan.

7. The method of claim 1 wherein said measured HU-value for said internal reference tissue or air is a mean value, a mode value, or a median value.

8. The method of claim 1, wherein said region of interest comprises one or more tissues selected from the group consisting of bone, cortical bone, trabecular or cancellous bone, fat, blood, marrow, muscle, white matter, gray matter, brain, spinal cord, spleen, liver, and combinations thereof.

9. A method for calibrating a CT scan for a current patient that utilizes a set of pre-determined values of an equivalent-density parameter for one or more internal reference tissues, said set including values obtained previously for a plurality of prior patients without the use of a calibration phantom, the method comprising:
    (a) measuring an HU-value for one or more internal reference tissues from the CT scan of said current patient;
    (b) referencing a set of pre-determined values of an equivalent-density parameter for the one or more internal reference tissues, said set including values obtained previously for a plurality of prior patients without the use of a calibration phantom;

(c) assigning, from said set of pre-determined values of the equivalent-density parameter, a value of the equivalent-density parameter to each of the one or more internal reference tissues;

(d) calibrating the scan responsive to the one or more measured HU-values and the corresponding assigned equivalent-density values.

10. A computer-implemented method for providing a set of calibrated values of bone mineral density (BMD) for a region of interest of a bone in a CT scan of a patient, without the use of a calibration phantom, using a set of pre-determined values of equivalent-BMD for air and one internal reference tissue, the method comprising the steps of:

(a) specifying a particular pre-determined value of equivalent-BMD for said internal reference tissue;

(b) specifying a particular pre-determined value of equivalent-BMD for air;

(c) measuring, from the CT scan, an HU-value for said internal reference tissue;

(d) obtaining an HU-value for air;

(e) measuring a set of HU-values for the region of interest; and (f) converting, responsive to said HU-value measured in step (c), to said HU-value obtained in step (d), and to said particular pre-determined values, said set of measured HU-values for the region of interest into the set of calibrated values of BMD.

11. The method of claim 10 wherein said internal reference tissue comprises visceral fat located near a vertebral body or visceral fat located near a proximal femur or blood located near a vertebral body.

12. The method of claim 10 wherein said particular pre-determined values of equivalent-BMD are specified responsive to one or more parameters selected from the group consisting of a scanner, a scanner model, a scanner manufacturer, a scan-acquisition parameter, a patient factor, and combinations thereof.

13. The method of claim 10 wherein said values of equivalent-BMD are specified responsive to a specified effective energy of the CT scan.

14. The method of claim 10 wherein said HU-value for air includes a measurement of an HU-value of air measured from the CT scan.

15. The method of claim 10 wherein said HU-value for air includes a non-patient-measured pre-specified value for air.

16. The method of claim 10 wherein the region of interest includes a femur, tibia, vertebra, humerus, or any portion thereof.

17. The method of claim 10 wherein said calibrated values of BMD are used to assess for osteoporosis or any bone pathology.

18. The method of claim 10 wherein said converting step f) includes one or more uses selected from the group consisting of monitoring osteoporosis drug treatments over time; pre-operative orthopaedic surgical planning for hip, spine, or knee, including total joint replacement, spinal fusion, pedicle screw fixation, and fracture fixation of long bones; assessing a degree of fracture healing or bone fusion; and combinations thereof.

19. A computer-implemented method for providing a set of calibrated values of bone mineral density (BMD) for a region of interest of a bone in a CT scan of a patient, without the use of a calibration phantom, the method comprising:

(a) specifying, from a set of pre-determined values of equivalent-BMD for internal reference tissues, a particular pre-determined value of equivalent-BMD for an internal reference tissue;

(b) specifying, from a set of pre-determined values of equivalent-BMD for air, a particular pre-determined value of equivalent-BMD for air;

(c) measuring, from the CT scan, an HU-value for said internal reference tissue;

(d) obtaining an HU-value for air;

(e) measuring a set of HU-values for the region of interest; and (f) converting, responsive to said HU-value measured in step (c), to said HU-value obtained in step (d), and to said particular pre-determined values, said set of measured HU-values for the region of interest into the set of calibrated values of BMD.

20. The method of claim 19 wherein said internal reference tissue comprises visceral fat located near a vertebral body or visceral fat located near a proximal femur or blood located near a vertebral body.

21. The method of claim 19 wherein said particular pre-determined values of equivalent-BMD are specified responsive to one or more parameters selected from the group consisting of a scanner, a scanner model, a scanner manufacturer, a scan-acquisition parameter, a patient factor, and combinations thereof.

22. The method of claim 19 wherein one or more of said specified values of equivalent-BMD are chosen responsive to a specified effective energy of the CT scan.

23. The method of claim 19 wherein said HU-value for air includes a measurement of an HU-value of air measured from the CT scan.

24. The method of claim 19 wherein said HU-value for air includes a non-patient-measured pre-specified value for air.

25. The method of claim 19 wherein the region of interest includes a femur, tibia, vertebra, humerus, or any portion thereof.

26. The method of claim 19 wherein the set of calibrated values of BMD are used to assess for osteoporosis or any bone pathology.

27. The method of claim 19 wherein said converting step f) includes one or more uses selected from the group consisting of monitoring osteoporosis drug treatments over time; pre-operative orthopaedic surgical planning for hip, spine, or knee, including total joint replacement, spinal fusion, pedicle screw fixation, and fracture fixation of long bones; assessing a degree of fracture healing or bone fusion; and combinations thereof.

* * * * *